(12) United States Patent
Beachy et al.

(10) Patent No.: US 7,462,457 B2
(45) Date of Patent: Dec. 9, 2008

(54) IDENTIFICATION OF ACTIVATED RECEPTORS AND ION CHANNELS

(75) Inventors: Philip A. Beachy, Towson, MD (US); Jussi Taipale, Baltimore, MD (US)

(73) Assignee: Johns Hopkins University School of Medicine, Baltimore, MD (US)

( * ) Notice: Subject to any disclaimer, the term of this patent is extended or adjusted under 35 U.S.C. 154(b) by 256 days.

(21) Appl. No.: 09/943,641

(22) Filed: Aug. 30, 2001

(65) Prior Publication Data

US 2002/0157119 A1 Oct. 24, 2002

Related U.S. Application Data

(60) Provisional application No. 60/229,243, filed on Aug. 30, 2000.

(51) Int. Cl.
*C12Q 1/68* (2006.01)
*G01N 33/53* (2006.01)

(52) U.S. Cl. ............... 435/7.1; 435/6; 435/7.93; 435/440; 435/325; 435/69.1

(58) Field of Classification Search .......... 435/6, 435/7.1, 7.2, 7.21, 7.31, 7.32, 7.94, 465, 435/69.1, 70.1, 7.95
See application file for complete search history.

(56) References Cited

U.S. PATENT DOCUMENTS 5,683,884 A * 11/1997 Moore et al. ............. 435/7.1
5,891,646 A * 4/1999 Barak et al. ............. 435/7.2
5,981,833 A * 11/1999 Wise et al. ............. 800/271
6,051,386 A * 4/2000 Lerner et al. ............. 435/7.21

OTHER PUBLICATIONS

Herrick-Davis et. al. J. Neurochem. 69: 1138-1144, 1997.*
Parnot et al., Proc. Natl. Acad. Sci. 97: 7615-7620, 2000.*
Han, M. et al. Constitutive Activation of Opsin by Mutation of Methionine 257 on Transmembrane Helix 6. Biochemistry 37, 8253-8261 (1998).
Lu, D. et al. A Ligand-Mimetic Model for Constitutive Activation of the Melanocortin-1 Receptor. Mol. Endocrinol. 12, 592-604 (1998).
McWhinney, C. et al. Constitutively Active Mutants of the alpha1a- and the alpha 1b-Adrenergic Receptor Subtypes Reveal Coupling to Different Signaling Pathways and Physiological Responses in Rat Cardiac Myocytes. J. Biol. Chem. 275, 2087-2097 (Jan. 21, 2000).
Pauwels, P.J. and Wurch, T. Review: Amino Acid Domains Involved in Constitutive Activation of G-Protein-Coupled Receptors. Mol. Neurobiol. 17, 109-135 (1998).
Spalding, T.A. et al. Constitutive Activation of the m5 Muscarinic Receptor by a Series of Mutations at the Extracellular End of Transmembrane 6. Biochemistry 36, 10109-10116 (1997).
Sommers, C.M., et al., "A Limited Spectrum of Mutations Causes Constitutive Activation of Yeast Alpha-Factor Receptor," Biochemistry 39:6898-6909 (2000).

* cited by examiner

*Primary Examiner*—Robert Landsman
*Assistant Examiner*—Gyan Chandra
(74) *Attorney, Agent, or Firm*—DLA Piper LLP (US)

(57) ABSTRACT

The present invention related to methods and reagents for generating and using activating mutations of receptors and ion channels.

24 Claims, 2 Drawing Sheets

1 $\quad [R] \rightleftharpoons [R^*]$

2 $\quad [R] \rightleftharpoons [R^*] + [A] \rightleftharpoons [R^*A]$

3 $[IR] \rightleftharpoons [I] + [R] \rightleftharpoons [R^*] + [A] \rightleftharpoons [R^*A]$ 4 $\quad [R^a] \rightleftharpoons [R^{a*}]$ 5 $[IR^a] \rightleftharpoons [I] + [R^a] \rightleftharpoons [R^{a*}]$ 6 $\quad [R^*] + [D] \rightleftharpoons [R^*D]$
$\quad\quad\quad\quad\quad\quad\quad\downarrow \quad\quad\quad\quad *$
$\quad\quad\quad\quad\quad\quad\text{signal}$

Figure 1

```
                          SEQUENCE LISTING

<160> NUMBER OF SEQ ID NOS: 2

<210> SEQ ID NO 1
<211> LENGTH: 9
<212> TYPE: PRT
<213> ORGANISM: Homo sapiens

<400> SEQUENCE: 1

Leu Glu Lys Gln Arg Asp Lys Asn Glu
1               5

<210> SEQ ID NO 2
<211> LENGTH: 10
<212> TYPE: PRT
<213> ORGANISM: Homo sapiens

<400> SEQUENCE: 2

Leu Leu Leu Leu Gly Ala Gly Glu Ser Gly
1               5                   10
```

IDENTIFICATION OF ACTIVATED RECEPTORS AND ION CHANNELS

REFERENCE TO RELATED APPLICATIONS

This application claims priority to Provisional application No. 60/229,243, filed on Aug. 30, 2000, the specification of which is incorporated by reference herein.

BACKGROUND OF THE INVENTION

The search for agonists and antagonists of cellular receptors has been an intense area of research aimed at drug discovery due to the elegant specificity of these molecular targets. Being able to generate activating mutations in a receptor can be useful in many different ways. For instance, the superfamily of G-protein coupled receptors (GPCRs) represents one of the most important families of drug targets for the pharmaceutical industry. They are activated by a wide range of extracellular signals including small biogenic amines, large protein hormones, neuropeptides, chemokines, lipid-derived mediators and even proteases such as thrombin. They are also fundamental receptors for the sensory perception of light, taste and smell. Moreover, of the top 200 best selling prescription drugs, more than 20% interact with GPCRs, providing worldwide sales of over $20 billion.

GPCRs transduce their signals across the plasma membrane via an interaction with heterotrimeric G-proteins, and this leads to an activation of intracellular effectors such as adenylate cyclase or phospholipase C and subsequent generation of second messengers such as cAMP (cyclic adenosine-monophosphate) or calcium. These effects are amplified and transmitted down through a cascade of intracellular events leading eventually to the physiological response of the cell to the stimulus. The enormous diversity of receptors, G-proteins and effectors, together with the widespread distribution of receptors across many tissues, reflects the important role that this family of genes plays in regulating physiological and pathophysiological processes.

The characteristic "motif" of the GPCR family are the 7 distinct hydrophobic regions, each 20 to 30 amino acids in length, generally regarded as forming the transmembrane domains of these integral membrane proteins. Indeed, the alternative name for this family is that of "7TM receptors." There is little conservation of amino acid sequence across the entire superfamily of receptors, but key sequence motifs can be found within phylogenetically related subfamilies, and these motifs can be used to help classify new members.

Since the first cloning of a GPCR more than a decade ago, over a thousand members of the family have been cloned from a variety of different species. This includes more than 160 distinct sub-types of human receptor for which the natural ligand is known, as well as over 100 human-derived receptor sequences for which the cognate ligand remains to be identified. The sequence motifs exhibited by these "orphan" receptors places them firmly in the GPCR family, but they typically show very low sequence similarity to specific known receptors, generally less than 40%. They are distributed throughout the GPCR phylogenetic tree, and many show better sequence similarity to each other than to known GPCRs, suggesting that they may represent new subfamilies of receptors with distinct, possibly novel, ligands. The majority of orphan receptors have been derived as a result of large-scale DNA sequencing, and as the generation of genomic information continues to increase, so the number of orphan receptors identified in sequence databases continues to increase. There is considerable debate concerning the total number of GPCRs that exist in the human genome, and estimates vary widely from 400 up to 5000. According to the first draft of the entire human genome published as part of the Human Genome Project, there are 616 human GPCRs if only rhodopsin-class, secretin-class, and metabotropic glutamate-class GPCRs are included (J. Craig Venter et al., Table 19 in Science 291: 1304-51).

Indeed, the current human genome sequencing efforts are identifying vast numbers of DNA sequences that may encode receptors, in general, for which corresponding ligands have not yet been identified. In some circumstances, the physiological events in which these orphan receptors are involved are not yet known either, and reagents for elucidating the receptor's physiological function is of importance. In other instances, the receptor is known to play an important physiological role and thereby could provide a means for developing therapeutics for diseases in which these receptors play a role.

The overall strategy for characterizing orphan receptors is often referred to as a "reverse pharmacology" approach to distinguish if from more conventional drug discovery approaches. The conventional approach was historically initiated by the discovery of a biological activity for which the ligand responsible was identified and then used to characterize tissue pharmacology and physiological role. Subsequently, the ligand was used to clone its corresponding receptor for use as a drug target in high-throughput screening. The reverse approach starts with an orphan receptor of unknown function that is used as a "hook" to fish out its ligand. The ligand is then used to explore the biological and pathophysiological role of the receptor. High-throughput screening is initiated on the receptor in parallel with the biological characterization in order to develop antagonists that will help determine the therapeutic value of the receptor.

One of the many great challenges in biology and medicine is to decipher the function of orphan receptors and their mechanism of action. However, traditional efforts to identify ligands for orphan receptors can be inefficient because they involve methodical searches through likely tissue sources to identify the natural ligand for the orphan receptor of interest. There is currently a need to be able to activate a receptor without knowledge of its ligand in order to mimic the effects of ligand binding. Such activated systems can be used to develop functional cell-based and biochemical assays, e.g., for drug screening, as well as to better understand the signal transduction process into which receptor integrates.

Another aspect of receptor-mediated signaling is that constitutively activating mutations have been identified in members of virtually every receptor family. Moreover, such activating mutations have been implicated in a variety of pathological conditions.

To further illustrate, constitutively active G protein-coupled receptors (GPCRs) were first identified in chimeras of the $\alpha_1$- and $\beta_2$-adrenergic receptors. Ultimately, this effect was mapped to residues at the C-terminal end of the third intracellular loop, and, in particular, the replacement of an alanine at position 293 with any other residue was found to increase the basal activity of the receptor and enhance the affinity for ligand as much as 100 fold. After the identification of naturally occurring constitutively active MC1-Rs and rhodopsin molecules, activating mutations in GPCRs were found to be responsible for a diverse array of inherited as well as somatic genetic disorders including hyperfunctioning thyroid adenomas, autosomal dominant hyperthyroidism, familial precocious male puberty, mettaphyseal chondrodysplasia, familial hypoparathyroidism, and congenital night blindness.

While constitutively activating mutations have been found in virtually all domains of the GPCRs, some mechanistic similarities are commonly found. Many constitutively active receptors demonstrate a higher affinity for agonist and lower $EC_{50}$ for further activation. In some cases the increased affinity for agonist, but not antagonist, was dramatic, and the correlation between agonist efficacy and increased affinity in the constitutively active mutants led to a proposed modification of the ternary complex model for GPCR activation. The established model holds that agonist binding stabilizes the active conformation (R*G) of the receptor in a complex with G protein while antagonists typically bind equally well to R and R*. Based on the identification and characterization of constitutively active GPCRs, an extended or allosteric ternary complex model was proposed in which receptor, independent of ligand binding, is in equilibrium between an inactive and active conformation. Mutations that constitutively activate receptors are proposed to disrupt internal constraints in the receptors, make the receptors less conformationally constrained, and therefore decrease the energy required to reach the R* state. The model thus explains the increased affinity of agonists for constitutively active receptors, even in the absence of G protein, since constitutive activation results in a higher percentage of receptors in the high-affinity R* state.

Because of the prevalence of constitutively active mutants of GPCRs and other extracellular receptors, there is currently a need to be able to activate a receptor without knowledge of its ligand in order to study the mechanism of action by which activating mutants give rise to disease states.

SUMMARY OF THE INVENTION

The present invention makes available a rapid, effective assay for screening and identifying mutations in receptors or ion channels, especially cell surface receptors and ion channels, which give rise to constitutively activated signaling. The subject assay enable rapid generation and identification of such activating mutations (point or multiple mutations), e.g., by combinatorial or scanning mutagenesis at residues which are most likely to contribute to conformational changes in the mutant receptor that result in activation.

Moreover, the subject activated receptors and ion channels can be used to generate drug screening assays for testing agents for their ability to overcome the effects of the activating mutations, e.g., to identify potential antagonists of the mutated, and in some instances, wild-type receptor or ion channel. Such assays enable rapid screening of large numbers of compounds to identify those which antagonize receptor bioactivity. Moreover, understanding the signaling events downstream of an orphan receptor, e.g., to identify second messengers and transcriptional targets for use as reporters to detect activation of the receptor, can permit the design of assays using wild-type receptor and for identifying agonists.

One aspect of the invention provides a method for identifying constitutively activating mutations in a receptor or an ion channel, comprising:

(A) providing a library of coding sequences for potentially activating mutations of a candidate receptor or ion channel, which library is generated by replacing coding sequences for small or medium side-chain amino acids with coding sequences for large side-chain amino acids, wherein said small or medium side-chain amino acids are located in or proximate transmembrane segment(s) of the receptor or ion channel;

(B) expressing said library in host cells;

(C) measuring the activity of the encoded receptor or ion channels in said host cells;

(D) identifying those coding sequence(s) which encoded activated receptors or ion channels.

In one embodiment, the receptor is selected from the group consisting of: a growth factor receptor, a cytokine receptor, a chemokine receptor, and an multisubunit immune recognition receptor (MIRR). In a related embodiment, the receptor is an orphan receptor. In another related embodiment, the receptor is a receptor tyrosine kinase (RTK). In another related embodiment, the receptor is a multipass transmembrane receptor. More preferably, the multipass transmembrane receptor is a 7TM receptor selected from the group consisting of: a G-protein coupled receptor, a chemoattractant peptide receptor, a neuropeptide receptor, a light receptor, a neurotransmitter receptor, and a polypeptide hormone receptor. In another related embodiment, the ion channel is a ligand gated ion channel.

In one embodiment, the activity of the receptor or ion channel is measured directly by determining the level of second messengers generated in response to receptor or ion channel activation. In a related embodiment, the activity is measured indirectly via an indicator gene. The indicator gene can be an unmodified endogenous gene. The indicator gene can also be a heterologous reporter gene, the activation of the transcriptional regulatory element of which is directly or indirectly regulated by the receptor or ion channel. In one embodiment, the level of transcriptional activation of the indicator gene can be amplified by overexpressing one or more intermediate components of the signaling cascade leading to the activation of the indicator gene. In another embodiment, the sensitivity of the indicator gene is modified by manipulating the promoter sequence at the natural locus for the indicator gene. In another embodiment, the activity of the indicator gene is modified by manipulating the transcriptional regulatory sequence at the natural locus for the indicator gene. In another embodiment, the activity of the indicator gene is modified by replacing the transcriptional regulatory sequence of the endogenous indicator gene with that of a heterologous gene. In one embodiment, the transcriptional regulatory element is derived from that of immediate early genes. In another embodiment, the transcriptional regulatory element is derived from several heterologous genes. In one embodiment, the reporter gene encodes a gene product selected from the group consisting of: chloramphenicol acetyl transferase, beta-galactosidase, secreted alkaline phosphatase, a gene product which confers a growth signal, and a gene product for growth in media containing aminotriazole or canavanine.

In one embodiment, the small or medium side-chain amino acids are located at the interfaces between transmembrane helices. In another embodiment, the small or medium side-chain amino acids are selected from the group consisting of: glycine, alanine, and serine. In yet another embodiment, the small or medium side-chain amino acids are selected from the group consisting of: asparagine, aspartic acid, cysteine, proline, threonine and valine. In one embodiment, the large/bulky side-chain amino acids are selected from the group consisting of: tryptophane, leucine, histidine, threonine, and tyrosine. In another embodiment, the large side-chain amino acids are selected from the group consisting of: asparagine, cysteine, glutamine, isoleucine, methionine, phenylalanine, proline, and valine.

In one embodiment, the cell is a prokaryotic cell. In another embodiment, the cell is a eukaryotic cell. More preferably, the eukaryotic cell is a mammalian cell. In another embodiment, the cell is selected from the group consisting of: an avian cell, an insect cell, a yeast cell, and a plant cell. In a preferred embodiment, the cell is a pigment cell capable of dispersing or aggregating its pigment in response to an activated receptor or ion channel.

In one embodiment, the mutation is identified as an activating mutation if the activity of the mutant polypeptide increases by at least 2-fold, preferably 5-fold, 10-fold or even more when compared to the activity of the wild-type polypeptide.

Another aspect of the invention provides a method for identifying constitutively activating mutations in a multipass transmembrane receptor, comprising:

(A) providing a library of coding sequences for a multipass transmembrane receptor, which library includes variant sequences which differ from the wild-type sequence of the receptor by one or more point mutations in or proximate a transmembrane segment(s) of the receptor that replace a small or medium amino acid residue with a large amino acid residue;

(B) expressing said library in host cells;

(C) measuring the activity of the encoded multipass transmembrane receptor in said host cells;

(D) identifying those coding sequence(s) which encoded activated multipass transmembrane receptor.

Another aspect of the invention provides a method for identifying a target second messenger or downstream signaling component of a receptor or ion channel, comprising:

(A) identifying an activating mutation of a receptor or ion channel using the method of claim 1;

(B) expressing said activating mutation of a receptor or ion channel in host cells; and, (C) identifying one or more second messenger molecules or downstream signaling components whose level is higher or lower or which is modified as a consequence to expression of said activating mutation of said receptor or ion channel.

In one embodiment, the receptor is selected from the group consisting of: a growth factor receptor, a cytokine receptor, a chemokine receptor, and an multisubunit immune recognition receptor (MIRR). In another embodiment, the receptor is a multipass transmembrane receptor. In a preferred embodiment, the multipass transmembrane receptor is a 7TM receptor selected from the group consisting of: a G-protein coupled receptor, a chemoattractant peptide receptor, a neuropeptide receptor, a light receptor, a neurotransmitter receptor, and a polypeptide hormone receptor. In yet another embodiment, the receptor is a receptor tyrosine kinase (RTK).

Another aspect of the invention provides a method for identifying an antagonist of an activating mutation of a receptor or ion channel, comprising:

(A) translationally providing a constitutively active mutant of a receptor or ion channel in an environment, which active mutant includes one or more point mutation(s) in or proximate a transmembrane segment(s) of the receptor that replace a small or medium amino acid residue with a large amino acid residue;

(B) contacting the receptor or ion channel with a test agent;

(C) comparing the activity of the receptor or ion channel in the presence of the test agent with the activity of the receptor or ion channel in the absence of the test agent; and, (D) identifying the test agent as an antagonist of the activated receptor or ion channel if the activity of the receptor or ion channel in the presence of the test agent is lower than the activity of the receptor or ion channel in the absence of the test agent.

In one embodiment, the translationally providing step is performed in a cell. The cell can be a prokaryotic cell, or a eukaryotic cell. In another embodiment, the cell is selected from the group consisting of: a mammalian cell, an avian cell, an insect cell, a yeast cell, and a plant cell. In a preferred embodiment, the cell is a pigment cell capable of dispersing or aggregating its pigment in response to an activated receptor or ion channel.

In one embodiment, the test agent is a member of a library. The library can be selected from the group consisting of: a randomly synthesized polypeptide library, a semi-randomly synthesized polypeptide library, a cDNA encoded polypeptide library, a genomic DNA encoded polypeptide library, a synthetic chemical library, and a natural chemical compound library.

Another aspect of the present invention relates to the generation of transgenic animals, preferably non-human mammals, expressing the activated mutants discovered by the subject method. Such animals can be used, merely for illustration, as disease models to elucidate the etiology and pathology of a disorder, as well as to test potential antagonists or other therapeutic agents in vivo.

This aspect of the invention provides a method for generating a non-human transgenic animal which expresses at least one activating mutant(s) of a receptor or an ion channel, comprising the steps of: (A) identifying an activating mutant of a receptor or an ion channel using the method of claim 1; and, (B) generating a non-human transgenic animal expressing said activating mutant. In one embodiment, the transgenic animal is selected from the group consisting of: a mammal, an insect, and a yeast.

Another aspect of the invention provides a method for identifying a modulator of a receptor or ion channel, comprising:

(A) identifying an activating mutation of a receptor or ion channel using the method of claim 1;

(B) identifying one or more second messenger molecules or downstream signaling components whose level is higher or lower or which is modified as a consequence to expression of said activating mutation of said receptor or ion channel;

(C) contacting an environment expressing a wild-type receptor or ion channel with a test agent;

(D) comparing the level of target second messenger molecules or down stream signaling components identified in step (B) in the presence or absence of the test agent; and, (E) determining whether the test agent increases or decreases the level of the target second messenger.

Another aspect of the invention provides a method of conducting a pharmaceutical business, comprising:

(A) by the method of claim 38 or 48, identifying one or more agents which effects signaling by a cell-surface receptor or ion channel;

(B) conducting therapeutic profiling of said identified agent(s), or further analogs thereof, for efficacy and toxicity in animals; and, (C) formulating a pharmaceutical preparation including one or more agents identified in step (B) as having an acceptable therapeutic profile.

In one embodiment, the business method further comprises an additional step of establishing a distribution system for distributing the pharmaceutical preparation for sale. In a preferred embodiment, the business method further includes establishing a sales group for marketing the pharmaceutical preparation.

Another aspect of the invention provides a method of conducting a pharmaceutical business, comprising:
(A) by the method of claim 38 or 48, identifying one or more agents which effects signaling by a cell-surface receptor or ion channel;
(B) (optionally) conducting therapeutic profiling of the agent for efficacy and toxicity in animals; and,
(C) licensing, to a third party, the rights for further drug development of the target agent.

BRIEF DESCRIPTION OF THE DRAWINGS

FIG. 1. Two state description of seven transmembrane receptor function. In an unstimulated state (1) the receptor exists in equilibrium between active (R*) and inactive (R) states. (2) Agonist (A) binds specifically to the active state (R*) and through mass action activates the receptor by increasing the total concentration of activated receptor ([R*]+[R*A]). (3) Inverse agonist inactivates receptor analogously by binding specifically to the inactive state. (4) Mutation (Ra) activates the receptor by affecting the two-state equilibrium to increase the fraction of receptor in the active state. (5) Inverse agonist can inactivate activated receptor by mass action. (6) Downstream coupling inhibitor (D) inhibits receptor signaling by binding to receptor and inhibiting activation of downstream targets.

DETAILED DESCRIPTION OF THE INVENTION

I. Overview

Figure 2:
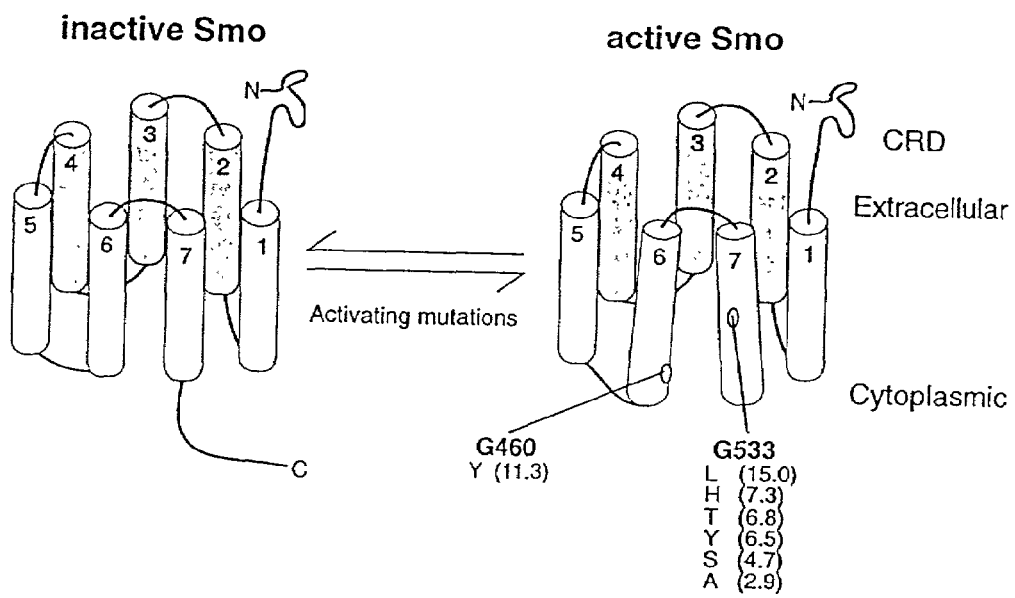
FIG. 2. Identification of Smoothened activating mutations at two glycines identified by the subject screening method. Activities of altered proteins are normalized to a value of 1 for wild-type Smoothened.

Proliferation, differentiation and death of eukaryotic cells are controlled by a variety of extracellular signals, such as hormones, neurotransmitters, and polypeptide factors. These diffusible ligands allow cells to influence and be influenced by environmental cues. The study of receptor activation has revealed a great deal of information about how cells respond to external stimuli, and this knowledge has led to the development of therapeutically important compounds.

The present invention makes available a rapid, effective assay for screening and identifying mutations in receptors or ion channels, especially cell surface receptors, which give rise to constitutively activated signaling. The subject assay enables rapid generation and identification of such activating mutations (point or multiple mutations), e.g., by combinatorial or scanning mutagenesis at residues which are most likely to contribute to conformational changes in the mutant receptor that result in activation. That is, in the case of 7TM receptors, the mutagenic approach is expected to give rise to forms of the receptor in which the steady-state equilibrium of the receptor is shifted towards the active form (R*) relative to the wild-type receptor.

To illustrate, seven transmembrane (7TM) receptors are thought to exist in two conformational states, active and inactive. In unstimulated cells, these states are in an equilibrium that strongly favors the inactive state (see FIG. 1). Agonists bind specifically to the active conformation of the receptor, increasing its concentration by mass action. Mutations exist that constitutively activate these receptors by destabilizing the inactive state, or by increasing the stability of the active state.

The present invention provides a systematic method of activating 7TM and other classes of cell surface receptors and ion channels. The strategy is based on systematically changing small residues (glycines, alanines and serines) found in transmembrane segments to larger residues. These small residues are preferred at the interfaces between transmembrane helices, e.g., be they intramolecular interactions such as in the case of multi-pass receptors and ions channels, or intermolecular interactions such as in the case of single pass receptors. Most mutations at these small residues will introduce side-chains that are substantially larger. These larger side-chains will then force the protein to adopt a different conformation, or prevent interaction with another molecule (e.g., a ligand or receptor subunit). The strategy involves generation of a set of libraries of mutant proteins where small residues at defined positions are changed to a number of other more bulky amino acid residues. The resulting library of mutants can be tested individually or in pools in biological assays to determine which substitutions induce constitutive activity. To illustrate, the library can be transfected into a host cell, and the activation of downstream second messengers or transcriptional targets thereof (reporter genes) can be detected.

Initial application of the subject method to four glycines in Smoothened has yielded eight activating mutants at two different sites (see FIG. 2). Our results indicate that this strategy may be used for rapid generation of activated forms of a large number of 7TM receptors, and suggests that the method can be applied to residues in the transmembrane regions of other classes of receptors and ion channels. In certain preferred embodiments, the receptor protein can be any receptor or ion channel which interacts with an extracellular molecule (i.e. hormone, growth factor, peptide, ion) to modulate a signal in the cell. In preferred embodiments, the receptor is a cell surface receptor, such as: a receptor tyrosine kinase, e.g., an EPH receptor; an ion channel; a cytokine receptor; an multi-subunit immune recognition receptor, a chemokine receptor; a growth factor receptor, a 7TM receptor (such as a G-protein coupled receptor, e.g., a chemoattractant peptide receptor, a neuropeptide receptor, a light receptor, a neurotransmitter receptor, or a polypeptide hormone receptor), a multipass transmembrane receptor.

Preferred G protein coupled receptors include α1A-adrenergic receptor, α1B-adrenergic receptor, α2-adrenergic receptor, α2B-adrenergic receptor, β1-adrenergic receptor, β2-adrenergic receptor, β3-adrenergic receptor, m1 acetylcholine receptor (AChR), m2 AChR, m3 AChR, m4 AChR, m5 AChR, D1 dopamine receptor, D2 dopamine receptor, D3 dopamine receptor, D4 dopamine receptor, D5 dopamine receptor, A1 adenosine receptor, A2b adenosine receptor, 5-HT1a receptor, 5-HT1b receptor, 5HT1-like receptor, 5-HT1d receptor, 5HT1d-like receptor, 5HT1d beta receptor, substance K (neurokinin A) receptor, fMLP receptor, fMLP-like receptor, angiotensin II type 1 receptor, endothelin ETA receptor, endothelin ET13 receptor, thrombin receptor, growth hormone-releasing hormone (GHRH) receptor, vasoactive intestinal peptide receptor, oxytocin receptor, somatostatin SSTR1 and SSTR2, SSTR3, cannabinoid receptor, follicle stimulating hormone (FSH) receptor, leutropin (LH/HCG) receptor, thyroid stimulating hormone (TSH) receptor, thromboxane A2 receptor, platelet-activating factor (PAF) receptor, C5a anaphylatoxin receptor, Interleukin 8 (IL-8) IL-8RA, IL-8RB, Delta Opioid receptor, Kappa Opioid receptor, mip-1/RANTES receptor, Rhodopsin, Red opsin, Green opsin, Blue opsin, metabotropic glutamate mGluR1-6, histamine H2 receptor, ATP receptor, neuropeptide Y receptor, amyloid protein precursor receptor, insulin-like growth factor II receptor, bradykinin receptor, gonadotropin-releasing hormone receptor, cholecystokinin receptor, prostaglandin receptor, melanocyte stimulating hormone receptor, antidiuretic hormone receptor, glucagon receptor, and adrenocorticotropic hormone II receptor.

The subject method is particularly well suited for analysis of transmembrane proteins whose biological function is gated by conformational changes (such as ligand gated ion channels). Accordingly, it is specifically contemplated that particularly preferred embodiments are where the receptor is a multipass transmembrane protein.

Moreover, the subject activated receptors and ion channels can be used to generate drug screening assays for testing agents for their ability to overcome the effects of the activating mutations, e.g., to identify potential antagonists of the mutated, and in some instances, wild-type receptor or ion channel. Such assays enable rapid screening of large numbers of compounds to identify compounds which antagonize receptor bioactivity. Moreover, understanding the signaling events downstream of an orphan receptor, e.g., to identify second messengers and transcriptional targets for use as reporters to detect activation of the receptor, can permit the design of assays using wild-type receptor and for identifying agonists.

Another aspect of the present invention relates to the generation of transgenic animals, preferably non-human mammals, expressing the activated mutants discovered by the subject method. Such animals can be used, merely for illustration, as disease models to elucidate the etiology and pathology of a disorder, as well as to test potential antagonists or other therapeutic agents in vivo.

II. Definitions

Before further description of the invention, certain terms employed in the specification, examples and appended claims are, for convenience, collected here.

"Activated," "activating" or "active" as used herein all refers to increased activity (biological, biochemical, etc.) as compared to wild-type. Generally, an activated receptor or ion channel exhibits a statistically significant increase of at least 10%, preferably 20%, 50%, 100%, 2-fold, 5-fold, 10-fold or more in activity when compared to its wild-type counterparts under certain assay conditions. The activity of a particular receptor or ion channel can be measured using any one or a combination of methods as outlined below.

"Agonists" and "antagonists" are molecules that modulate signal transduction via a receptor or ion channel. Agonists and one class of antagonists are capable of binding to the receptor, though not necessarily at the binding site of the natural ligand, and can modulate signal transduction when used alone (i.e. can be surrogate ligands, or can alter signal transduction in the presence of the natural ligand, either to enhance or inhibit signaling by the natural ligand). Another class of antagonists may not bind directly to the receptor. Rather, they act on one or more downstream target molecules of the activated receptor or ion channel, thereby modulating signal tranduction of the receptor or ion channel. For example, "antagonists" can be molecules that block or decrease the signal transduction activity of receptor, e.g., they can competitively, noncompetitively, and/or allosterically inhibit signal transduction from the receptor, whereas "agonists" potentiate, induce or otherwise enhance the signal transduction activity of a receptor. The terms "receptor activator" and "surrogate ligand" refer to an agonist which induces signal transduction from a receptor.

As used herein, "cell surface receptor" refers to molecules that occur on the surface of cells, interact with the extracellular environment, and transmit or transduce the information regarding the environment intracellularly in a manner that may modulate intracellular second messenger activities or transcription of specific promoters, resulting in transcription of specific genes.

The term "compound" as used herein is meant to include, but is not limited to, peptides, nucleic acids, carbohydrates, small organic molecules, and natural product extract libraries.

As used herein, "extracellular signals" include a molecule or a change in the environment that is transduced intracellularly via cell surface proteins that interact, directly or indirectly, with the signal. An extracellular signal or effector molecule includes any compound or substance that in some manner alters the activity of a cell surface protein. Examples of such signals include, but are not limited to, molecules such as acetylcholine, growth factors and hormones, lipids, sugars and nucleotides that bind to cell surface and/or intracellular receptors and ion channels and modulate the activity of such receptors and channels. The term "extracellular signals" also include as yet unidentified substances that modulate the activity of a cellular receptor, and thereby influence intracellular functions. Such extracellular signals are potential pharmacological agents that may be used to treat specific diseases by modulating the activity of specific cell surface receptors.

As used herein, "heterologous DNA" or "heterologous nucleic acid" include DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes test polypeptides, receptors, reporter genes, transcriptional and translational regulatory sequences, selectable or traceable marker proteins, such as a protein that confers drug resistance.

The term "indicator gene" generically refers to an expressible (e.g., able to be transcribed and (optionally) translated) DNA sequence which is expressed in response to a signal transduction pathway modulated by a target receptor or ion channel. Exemplary indicator genes include unmodified endogenous genes of the host cell, modified endogenous genes, or a reporter gene of a heterologous construct, e.g., as part of a reporter gene construct.

The term "modulation of a signal transduction activity of a receptor protein" in its various grammatical forms, as used herein, designates induction and/or potentiation, as well as inhibition of one or more signal transduction pathways downstream of a receptor.

"Orphan receptors" is a designation given to receptors for which no specific natural ligand has been described and/or for which no function has been determined.

The terms "protein", "polypeptide" and "peptide" are used interchangeably herein.

The term "proximate transmembrane segment" is used to describe amino acids located at a position in the polypeptide in which it influences the structure of a transmembrane segment of the receptor or ion channel. In certain embodiments, such positions are within 25 amino acids, and more preferably within 20 residues, 15 residues, or 10 residues, and most preferably within 5 residues of the first or last reside of the transmembrane segment(s).

As used herein, "recombinant cells" include any cells that have been modified by the introduction of heterologous DNA. Control cells include cells that are substantially identical to the recombinant cells, but do not express one or more of the proteins encoded by the heterologous DNA, e.g., do not include or express the reporter gene construct, receptor or test polypeptide.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, a "reporter gene construct" is a nucleic acid that includes a "reporter gene" operatively linked to at least one transcriptional regulatory sequence. Transcription of the reporter gene is controlled by these sequences to which they are linked. The activity of at least one or more of these control sequences is directly or indirectly regulated by the target receptor protein. Exemplary transcriptional control sequences are promoter sequences. A reporter gene is meant to include a promoter-reporter gene construct which is heterologously expressed in a cell.

"Signal transduction" is the processing of physical or chemical signals from the cellular environment through the cell membrane, and may occur through one or more of several mechanisms, such as activation/inactivation of enzymes (such as proteases, or other enzymes which may alter phosphorylation patterns or other post-translational modifications), activation of ion channels or intracellular ion stores, effector enzyme activation via guanine nucleotide binding protein intermediates, formation of inositol phosphate, activation or inactivation of adenylyl cyclase, direct activation (or inhibition) of a transcriptional factor and/or activation.

"Small side-chain amino acids" as used herein refers to amino acids having small volume side chains, such as Ala, Gly and Ser.

"Medium side-chain amino acids" as used herein refers to amino acids having medium volume side chains, such as Asn, Asp, Cys, Pro, Thr and Val.

"Large/bulky side-chain amino acids" as used herein refers to amino acids having large volume side chains, such as Arg, Glu, Gln, His, Ile, Leu, Lys, Met, Phe, Trp and Tyr.

In certain embodiments of the subject the replacement strategy, the small or medium side-chain amino acids (residues being replaced) are either amino acids with small side-chains (Ala, Gly or Ser) or residues with small or medium hydrophobic side-chains (Ala, Gly, Pro and Val). Similarly, in a preferred variation to this strategy, the large/bulky amino acids (replacement residues) include amino acids with medium to large, neutral side-chains (Asn, Cys, Gln, His, Ile, Leu, Met, Phe, Pro, Thr, Trp, Tyr, Val). That is, the replacement is conservative with respect to charge but not steric considerations. For instance, in one embodiment, amino acid residues having small side-chains and located in or near a transmembrane domain are replaced with amino acids with medium to large, neutral side-chains. Preferably, Gly and Ala residues, and optionally Ser residues, are targeted.

"Statistically significant" as used herein means that quantitative measurements of certain activities, either biological or biochemical or both, are statistically significantly different from one sample to the other. Preferably, an activating mutation will cause an increase in activity of 50%, more preferably, 2-fold, 5-fold, 10 fold or more when compared to the wild-type polypeptide. Likewise, an antagonist of an activated receptor or an ion channel will cause a statistically significant decrease in activity of at least 20%, more preferably 50%, 75%, 90%, 95% or even 99%.

III. Exemplary Embodiments

The subject assays provide a means for identifying activating mutations in transmembrane receptors and ion channels. In general, the various mutant proteins are expressed in a host cell, the ability of a given set of mutations to activate. the signal transduction activity of the target receptor is scored for by up or down-regulation of a detection signal. Second messenger generation via the receptor can be measured in a variety of ways. For example, second messenger generation can be detected directly. Alternatively, the use of a reporter gene can provide a convenient readout. The present invention also provides for a number of other detection means, such as indicator genes. By whatever means measured, a statistically significant change in the detection signal can be used to facilitate isolation of those cells from a mixture which have received a signal via an activated target receptor, and thus can be used to isolate the coding sequence for that mutant.

In general the host cells will express recombinant genes encoding the receptor or ion channel of interest. In certain instances, it may be desirable to inactivate one or more endogenous genes of the host cells. For example, certain preferred embodiments in which a heterologous receptor is provided utilize host cells in which the gene for the homologous receptor has been inactivated. Likewise, other proteins involved in transducing signals from the target receptor can be inactivated, or complemented with an ortholog or paralog from another organism, e.g., yeast G protein subunits can be complemented by mammalian G protein subunits in yeast cells also engineered to express a mammalian G protein coupled receptor. Other complementations include, for example, expression of heterologous MAP kinases or ERK kinases, MEKs or MKKs (MAP kinase kinases), MEKKs (MEK kinases), ras, raf, STATs, JAKs and the like.

In certain embodiments the subject assays measure the production of second messengers to determine changes in ligand engagement by the receptor. In preferred embodiments, changes in GTP hydrolysis, calcium mobilization, or phospholipid hydrolysis can be measured.

In other embodiments the assay cells contain an indicator gene. For instance, the host cell can harbor a reporter construct containing a reporter gene in operative linkage with one or more transcriptional regulatory elements responsive to the signal transductin activity of the receptor protein. Exemplary reporter genes include enzymes, such as luciferase, phosphatase, or β-galactosidase which can produce a spectrometrically active label, e.g., changes in color, fluorescence or luminescence, or a gene product which alters a cellular phenotype, e.g., cell growth, drug resistance or auxotrophy. In preferred embodiments: the reporter gene encodes a gene product selected from the group consisting of chloramphenicol acetyl transferase, beta-galactosidase and secreted alkaline phosphatase; the reporter gene encodes a gene product which confers a growth signal; the reporter gene encodes a gene product for growth in media containing aminotriazole or canavanine.

In developing the subject assays, it was recognized that a frequent result of receptor-mediated responses to activating signals was the transcriptional activation or inactivation of specific genes. Thus, transcription of genes controlled by receptor-responsive transcriptional elements often reflects the activity of the surface protein by virtue of transduction of an intracellular signal. To illustrate, with the wild-type receptor, the intracellular signal that is transduced can be initiated by the specific interaction of the receptor with an extracellular signal, particularly a ligand. This interaction sets in motion a cascade of intracellular events, the ultimate consequence of which is a rapid and detectable change in the transcription or translation of a gene. By selecting transcriptional regulatory sequences that are responsive to the transduced intracellular signals and operatively linking the selected promoters to indicator genes, whose transcription or translation is readily detectable and measurable, a transcription based assay provides a rapid indication of whether a mutation gives rise to an activated receptor or ion channel that modulates intracellular transduction.

Indicator gene based assays of this invention measure the end stage of the above described cascade of events, e.g., transcriptional modulation. Accordingly, in practicing one embodiment of the assay, a reporter gene construct is inserted into the reagent cell in order to generate a detection signal dependent on receptor signaling. Typically, the reporter gene construct will include a reporter gene in operative linkage with one or more transcriptional regulatory elements responsive to the signal transduction activity of the target receptor, with the level of expression of the reporter gene providing the receptor-dependent detection signal. As described below, certain endogenous genes can also act as indicator genes, e.g., provide a detectable signal in response to a signal transduction from a receptor or ion channel. In either embodiment, the amount of transcription from the indicator gene may be measured using any method known to those of skill in the art to be suitable. For example, specific mRNA expression may be detected using Northern blots or specific protein product may be identified by a characteristic stain or an intrinsic activity.

In preferred embodiments, the gene product of the indicator gene is detected by an intrinsic activity associated with that product. For instance, the indicator gene may encode a gene product that, by enzymatic activity, gives rise to a detection signal based on, for example, color, fluorescence, or luminescence.

The amount of expression from the indicator gene is then compared to the amount of expression when the wild-type receptor is expressed. Any statistically or otherwise significant difference in the amount of transcription indicates that a given mutation has in some manner altered the activity of the specific receptor or ion channel.

In other preferred embodiments, the indicator gene provides a selection method such that cells in which activation of one or more signal pathways of a receptor or ion channel provides a growth advantage to the treated cell. For example, expression of the indicator gene could enhance cell viability, relieve a cell nutritional requirement, and/or provide resistance to a drug.

In other embodiments, changes in intracellular second messenger pathways can be detected biochemically rather than biologically. For example, changes in intracellular $Ca^{+2}$, phosphorylation states of proteins, activities of intracellular enzymes, and the like can be detected. Still other detection techniques include microphysiometric devices which permit detection of small changes in, e.g., ions or intracellular pH.

Any transfectable cell that can express the desired cell surface protein in a manner such that the protein functions to intracellularly transduce an extracellular signal may be used. Similarly, any cell surface protein that is known to those of skill in the art or that may be identified by those of skill in the art may be used in the assay.

A. Host Cells

Any transfectable cell that can express the desired cell surface protein in a manner such that the protein functions to intracellularly transduce an extracellular signal may be used. Similarly, any cell surface protein that is known to those of skill in the art or that may be identified by those of skill in the art may used in the assay. The cell surface protein may be endogenously expressed on the selected cell or it may be expressed from cloned DNA.

Suitable host cells for generating the subject assay include prokaryotes, yeast, or higher eukaryotic cells, including plant and animal cells, especially mammalian cells. Prokaryotes include gram negative or gram positive organisms. Examples of suitable mammalian host cell lines include the COS-7 line of monkey kidney cells (ATCC CRL 1651) (Gluzman et al., Cell 23: 175, 1981), CV-1 cells (ATCC CCL 70), L cells, C127, 3T3, Chinese hamster ovary (CHO), HeLa, HEK-293, SWISS 3T3, and BHK cell lines.

In certain of the embodiments described below, e.g., where pigment dispersion or aggregation is detected, the host cell is a pigment cell line capable of dispersing or aggregating its pigment in response to an activate receptor or ion channel. For instance, the host cell can be a melanophore. Cultures of melanophores have been obtained. Continuous long term cultures of melanophores have been established. See, for example, Ide (1974) Developmental Biology 41: 380-384; and Daniolos et al. (1990), Pigment Cell Research 3: 38-43.

If yeast cells are used, the yeast may be of any species which are cultivable and in which an exogenous receptor can be made to engage the appropriate signal transduction machinery of the host cell. Suitable species include *Kluyverei lactis, Schizosaccharomyces pombe*, and *Ustilaqo maydis; Saxxharomyces cerevisiae* is preferred. Other yeast which can be used in practicing the present invention are *Neurospora crassa, Aspergillus niger, Aspergillus nidulans, Pichia pastoris, Candida tropicalis*, and *Hansenula polymorpha*. The term "yeast", as used herein, includes not only yeast in a strictly taxonomic sense, i.e., unicellular organisms, but also yeast-like multicellular fungi or filamentous fungi.

The choice of appropriate host cell will also be influenced by the choice of detection signal. For instance, reporter constructs, as described below, can provide a selectable or screenable trait upon transcriptional activation (or inactivation) in response to a signal transduction pathway coupled to the target receptor. The reporter gene may be an unmodified gene already in the host cell pathway, such as the genes responsible for growth arrest in yeast. It may be a host cell gene that has been operably linked to a "receptor-responsive" promoter. Alternatively, it may be a heterologous gene (e.g., a "reporter gene construct") that has been so linked. Suitable genes and promoters are discussed below. In other embodiments, second messenger generation can be measured directly in the detection step, such as mobilization of intracellular calcium or phospholipid metabolism are quantitated. In yet other embodiments indicator genes can be used to detect receptor-mediated signaling.

Accordingly, it will be understood that to achieve selection or screening, the host cell must have an appropriate phenotype. For example, generating a pheromone-responsive chimeric HIS3 gene in a yeast that has a wild-type HIS3 gene would frustrate genetic selection. Thus, to achieve nutritional selection, an auxotrophic strain is wanted.

A variety of complementations for use in the subject assay can be constructed. Indeed, many yeast genetic complementations with mammalian signal transduction proteins have been described in the art. For example, Mosteller et al. (Mol. Cell Biol. 14: 1104-1112, 1994) demonstrates that human Ras proteins can complement loss of ras mutations in *S. cerevisiae*. Moreover, Toda et al. (Princess Takamatsu Symp 17: 253-60, 1986) have shown that human ras proteins can complement the loss of RAS1 and RAS2 proteins in yeast, and hence are functionally homologous. Both human and yeast RAS proteins can stimulate the magnesium and guanine nucleotide-dependent adenylate cyclase activity present in yeast membranes. Ballester et al. (Cell 59: 681-6, 1989) describe a vector to express the mammalian GAP protein in the yeast *S. cerevisiae*. When expressed in yeast, GAP inhibits the function of the human ras protein, and complements the loss of IRA1. IRA1 is a yeast gene that encodes a protein with homology to GAP and acts upstream of RAS. Mammalian GAP can therefore function in yeast and interact with yeast RAS. Wei et al. (1994) Gene 151: 279-84 describes that a human Ras-specific guanine nucleotide-exchange factor, Cdc25GEF, can complement the loss of CDC25 function in *S. cerevisiae*. Martegani et al. (EMBO J 11: 2151-7, 1992) describe the cloning by functional complementation of a mouse cDNA encoding a homolog of CDC25, a *Saccharomyces cerevisiae* RAS activator. Vojtek et al. (J. Cell Sci. 105: 777-85, 1993) and Matviw et al. (Mol Cell Biol 12: 5033-40, 1992) describe how a mouse CAP protein, e.g., an adenylyl cyclase associated protein associated with ras-mediated signal transduction, can complements defects in *S. cerevisiae*. Papasavvas et al. (Biochem Biophys Res Commun 184: 1378-85, 1992) also suggest that inactivated yeast adenyl cyclase can be complemented by a mammalian adenyl cyclase gene. Hughes et al. (Nature 364: 349-52, 1993) describe the complementation of byrl in fission yeast by mammalian MAP kinase kinase (MEK). Parissenti et al. (Mol Cell Endocrinol 98: 9-16, 1993) describes the reconstitution of bovine protein kinase C (PKC) in yeast. The $Ca^{2+}$- and phospholipid-dependent Ser/Thr kinase PKC plays important roles in the transduction of cellular signals in mammalian cells. Marcus et al. (PNAS 92: 6180-4, 1995) suggests the complementation of shk1 null mutations in *S. pombe* by the either the structurally related *S. cerevisiae* Ste20 or mammalian p65PAK protein kinases.

"Inactivation", with respect to genes of the host cell, means that production of a functional gene product is prevented or inhibited. Inactivation may be achieved by deletion of the gene, mutation of the promoter so that expression does not occur, or mutation of the coding sequence so that the gene product is inactive. Inactivation may be partial or total.

"Complementation", with respect to genes of the host cell, means that at least partial function of inactivated gene of the host cell is supplied by an exogenous nucleic acid. For instance, yeast cells can be "mammalianized", and even "humanized", by complementation of receptor and signal transduction proteins with mammalian homologs. To illustrate, inactivation of a yeast Byr2/Stel 1 gene can be complemented by expression of a human MEKK gene.

B. Generating Mutational Libraries

There are many ways by which the gene library of mutants can be generated, particularly by the use of degenerate oligonucleotide sequences (in the case of cassette mutagenesis). In one embodiment, the entire coding sequence, or at least that portion which is to be mutagenized, is synthesized, e.g., using automatic DNA synthesizer, and the synthetic genes or fragments thereof are then ligated into an appropriate gene for expression. The purpose of a degenerate set of genes is to provide, in one mixture, all of the sequences encoding the desired set of potential sequences. The synthesis of degenerate sequences is well known in the art (see for example, Narang, S A (1983) Tetrahedron 39: 3; Itakura et al. (1981) Recombinant DNA, Proc 3rd Cleveland Sympos. Macromolecules, ed. A G Walton, Amsterdam: Elsevier pp. 273-289; Itakura et al. (1984) Annu. Rev. Biochem. 53: 323; Itakura et al. (1984) Science 198: 1056; Ike et al. (1983) Nucleic Acid Res. 11: 477. Such techniques have been employed in the directed evolution of other proteins (see, for example, Scott et al. (1990) Science 249: 386-390; Roberts et al. (1992) PNAS 89: 2429-2433; Devlin et al. (1990) Science 249: 404-406; Cwirla et al. (1990) PNAS 87: 6378-6382; as well as U.S. Pat. Nos. 5,223,409, 5,198,346, and 5,096,815).

To continue the illustration, the coding sequence for the receptor or ion channel is analyzed and residues targeted for mutagenesis are identified. In an embodiment of a "selective strategy", only selected residues (e.g., all amino acids with small side-chains), and preferably only those occurring in the transmembrane domain(s) of the protein, are mutagenized. Alternatively, a more random approach might be taken wherein random (indiscriminate) mutations throughout the transmembrane domain(s) are introduced (such as by PCR-mediated mutagenesis).

Moreover, the mutations which are introduced may be random, e.g., any of the 20 amino acids, or selective, e.g., residues which are intended to alter the steric and/or electronic (including charge) nature of the side-chain at the site of mutation. In one embodiment of the selective strategy, the residues which are to mutagenized in the TM domains are those which are characterized as small or medium sized amino acid residues (e.g., Ala, Gly and Ser for small, and Asn, Asp, Cys, Pro, Thr and Val for medium), and the replacement residues include amino acids with large side-chains (e.g., Arg, Glu, Gln, His, Ile, Leu, Lys, Met, Phe, Trp and Tyr). In a preferred variation to this strategy, the residues being replaced are either amino acids with small side-chains (Ala, Gly or Ser) or residues with small or medium hydrophobic side-chains (Ala, Gly, Pro and Val). In a preferred variation to this strategy, the replacement residues include amino acids with medium to large, neutral side-chains (Asn, Cys, Gln, His, Ile, Leu, Met, Phe, Pro, Thr, Trp, Tyr, Val). That is, the replacement is conservative with respect to charge but not steric considerations. For instance, in one embodiment, amino acid residues having small side-chains and located in or near a transmembrane domain are replaced with amino acids with medium to large, neutral side-chains. Preferably, Gly and Ala residues, and optionally Ser residues, are targeted.

The mutagenic approach can be designed to provide libraries of single point mutations, but will more preferably be representative of the possible permutations of mutations ranging from single to multiple site mutations. For instance, where there are three sites to be mutagenized into one of 13 different residues, then there are 39 possible single point mutations, 507 possible double mutations and 2197 possible triple mutations—for a total of 2743 permutations.

In preferred embodiments, the receptor library includes at least 10 different polypeptides, though more preferably at least $10^2$, $10^3$, $10^4$, or even $10^5$ different permutations.

C. Expression Systems

Ligating a polynucleotide coding sequence into a gene construct, such as an expression vector, and transforming or transfecting into hosts, either eukaryotic (yeast, avian, insect or mammalian) or prokaryotic (bacterial cells), are standard procedures used in producing other well-known proteins, including sequences encoding exogenous receptors and ion channels. Similar procedures, or modifications thereof, can be employed to prepare recombinant reagent cells of the present invention by tissue-culture technology in accord with the subject invention.

In general, it will be desirable that the vector be capable of replication in the host cell. It may be a DNA which is integrated into the host genome, and thereafter is replicated as a part of the chromosomal DNA, or it may be DNA which replicates autonomously, as in the case of a plasmid. In the latter case, the vector will include an origin of replication which is functional in the host. In the case of an integrating vector, the vector may include sequences which facilitate integration, e.g., sequences homologous to host sequences, or encoding integrases.

Appropriate cloning and expression vectors for use with bacterial, fungal, yeast, and mammalian cellular hosts are known in the art, and are described in, for example, Powels et al. (Cloning Vectors: A Laboratory Manual, Elsevier, N.Y., 1985). Mammalian expression vectors may comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a poly-adenylation site, splice donor and acceptor sites, and transcriptional termination sequences.

The preferred mammalian expression vectors contain both prokaryotic sequences, to facilitate the propagation of the vector in bacteria, and one or more eukaryotic transcription units that are expressed in eukaryotic cells. The pcDNAI/amp, pcDNAI/neo, pRc/CMV, pSV2gpt, pSV2neo, pSV2-dhfr, pTk2, pRSVneo, pMSG, pSVT7, pko-neo and pHyg derived vectors are examples of mammalian expression vectors suitable for transfection of eukaryotic cells. Some of these vectors are modified with sequences from bacterial plasmids, such as pBR322, to facilitate replication and drug resistance selection in both prokaryotic and eukaryotic cells. Alternatively, derivatives of viruses such as the bovine papillomavirus (BPV-1), or Epstein-Barr virus (pHEBo, pREP-derived and p205) can be used for transient expression of proteins in eukaryotic cells. The various methods employed in the preparation of the plasmids and transformation of host organisms are well known in the art. For other suitable expression systems for both prokaryotic and eukaryotic cells, as well as general recombinant procedures, see Molecular Cloning: A Laboratory Manual, 2nd Ed., ed. by Sambrook, Fritsch and Maniatis (Cold Spring Harbor Laboratory Press: 1989) Chapters 16 and 17.

The transcriptional and translational control sequences in expression vectors to be used in transforming mammalian cells may be provided by viral sources. For example, commonly used promoters and enhancers are derived from Polyoma, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide the other genetic elements required for expression of a heterologous DNA sequence. The early and late promoters are particularly useful because both are obtained easily from the virus as a fragment which also contains the SV40 viral origin of replication (Fiers et al., Nature 273: 111, 1978). Smaller or larger SV40 fragments may also be used, provided the approximately 250 bp sequence extending from the Hind III site toward the Bgl I site located in the viral origin of replication is included. Exemplary vectors can be constructed as disclosed by Okayama and Berg (Mol. Cell Biol. 3: 280, 1983). A useful system for stable high level expression of mammalian receptor cDNAs in C127 murine mammary epithelial cells can be constructed substantially as described by Cosman et al. (Mol. Immunol. 23: 935, 1986). Other expression vectors for use in mammalian host cells are derived from retroviruses.

In other embodiments, the use of viral transfection can provide stably integrated copies of the expression construct. In particular, the use of retroviral, adenoviral or adeno-associated viral vectors is contemplated as a means for providing a stably transfected cell line which expresses an exogenous receptor, and/or a polypeptide library.

A number of vectors exist for the expression of recombinant proteins in yeast. For instance, YEP24, YIP5, YEP51, YEP52, pYES2, and YRP17 are cloning and expression vehicles useful in the introduction of genetic constructs into *S. cerevisiae* (see, for example, Broach et al. (1983) in Experimental Manipulation of Gene Expression, ed. M. Inouye Academic Press, p. 83, incorporated by reference herein). These vectors can replicate in *E. coli* due the presence of the pBR322 ori, and in *S. cerevisiae* due to the replication determinant of the yeast 2 micron plasmid. In addition, drug resistance markers such as ampicillin can be used. Moreover, if yeast are used as a host cell, it will be understood that the expression of a gene in a yeast cell requires a promoter which is functional in yeast. Suitable promoters include the promoters for metallothionein, 3-phosphoglycerate kinase (Hitzeman et al., J. Biol. Chem. 255, 2073 (1980) or other glycolytic enzymes (Hess et al., J. Adv. Enzyme Req. 7, 149 (1968); and Holland et al. Biochemistry 17, 4900 (1978)), such as enolase, glyceraldehyde-3-phosphate dehydrogenase, hexokinase, pyruvate decarboxylase, phospho-fructokinase, glucose-6-phosphate isomerase, 3-phosphoglycerate mutase, pyruvate kinase, triosephosphate isomerase, phospho-glucose isomerase, and glucokinase. Suitable vectors and promoters for use in yeast expression are further described in R. Hitzeman et al., EPO Publication. No. 73,657. Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. Finally, promoters that are active in only one of the two haploid mating types may be appropriate in certain circumstances. Among these haploid-specific promoters, the pheromone promoters MFα1 and MFa1 are of particular interest.

In some instances, it may be desirable to derive the host cell using insect cells. In such embodiments, recombinant polypeptides can be expressed by the use of a baculovirus expression system. Examples of such baculovirus expression systems include pVL-derived vectors (such as pVL1392, pVL1393 and pVL941), pAcUW-derived vectors (such as pAcUWI), and pBlueBac-derived vectors (such as the 13-Gal containing pBlueBac III).

In constructing suitable expression plasmids, the termination sequences associated with these genes, or with other genes which are efficiently expressed in the host cell, may also be ligated into the expression vector 3' of the heterologous coding sequences to provide polyadenylation and termination of the mRNA.

D. Seven Transmembrane Receptors.

In certain embodiments, the subject method is applied to the discovery of activating mutations in the 7TM family.

In particular, many different 7TM receptors are known to interact with G proteins. G protein signaling systems include three components: the receptor itself, a GTP-binding protein (G protein), and an intracellular target protein. The cell membrane acts as a switchboard. Messages arriving through different receptors can produce a single effect if the receptors act on the same type of G protein. On the other hand, signals activating a single receptor can produce more than one effect if the receptor acts on different kinds of G proteins, or if the G proteins can act on different effectors.

In their resting state, the G proteins, which consist of alpha (α), beta (β) and gamma (γ) subunits, are complexed with the nucleotide guanosine diphosphate (GDP) and are in contact with receptors. When a hormone or other first messenger binds to receptor, the receptor changes conformation and this alters its interaction with the G protein. This spurs the α subunit to release GDP, and the more abundant nucleotide guanosine triphosphate (GTP), replaces it, thus activating the G protein. The G protein then dissociates to separate the α subunit from the still complexed β and γ subunits. Either the Gα subunit, or the Gβγ complex, depending on the pathway, interacts with an effector. The effector (which is often an enzyme) in turn converts an inactive precursor molecule into an active "second messenger," which may diffuse through the cytoplasm, triggering a metabolic cascade. After a few seconds, the Gα converts the GTP to GDP, thereby inactivating itself. The inactivated Gα may then reassociate with the Gβγ complex.

Hundreds, if not thousands, of receptors convey messages through heterotrimeric G proteins, of which at least 17 distinct forms have been isolated. Although the greatest variability has been seen in the α subunit, several different β and γ structures have been reported. There are, additionally, several different G protein-dependent effectors.

Most G protein-coupled receptors are comprised of a single protein chain that is threaded through the plasma membrane seven times. Such receptors are often referred to as seven-transmembrane receptors (STRs). More than a hundred different STRs have been found, including many distinct receptors that bind the same ligand, and there are likely many more STRs awaiting discovery.

In addition, STRs have been identified for which the natural ligands are unknown; these receptors are termed "orphan" G protein-coupled receptors, as described above. Examples include receptors cloned by Neote et al. (Cell 72: 415, 1993); Kouba et al. (FEBS Lett. 321: 173, 1993); Birkenbach et al. (J. Virol. 67: 2209, 1993).

The "exogenous receptors" of the present invention may be any G protein-coupled receptor which is exogenous to the cell which is to be genetically engineered for the purpose of the present invention. This receptor may be a plant or animal cell receptor. Screening for binding to plant cell receptors may be useful in the development of, e.g., herbicides. In the case of an animal receptor, it may be of invertebrate or vertebrate origin. If an invertebrate receptor, an insect receptor is preferred, and would facilitate development of insecticides. The receptor may also be a vertebrate, more preferably a mammalian, still more preferably a human, receptor. The exogenous receptor is also preferably a seven transmembrane segment receptor.

Known ligands for G protein coupled receptors include: purines and nucleotides, such as adenosine, cAMP, ATP, UTP, ADP, melatonin and the like; biogenic amines (and related natural ligands), such as 5-hydroxytryptamine, acetylcholine, dopamine, adrenaline, adrenaline, adrenaline., histamine, noradrenaline, noradrenaline, noradrenaline, tyramine/octopamine and other related compounds; peptides such as adrenocorticotrophic hormone (aeth), melanocyte stimulating hormone (msh), melanocortins, neurotensin (nt), bombesin and related peptides, endothelins, cholecystokinin, gastrin, neurokinin b (nk3), invertebrate tachykinin-like peptides, substance k (nk2), substance p (nk1), neuropeptide y (npy), thyrotropin releasing-factor (trf), bradykinin, angiotensin II, beta-endorphin, c5a anaphalatoxin, calcitonin, chemokines (also called intercrines), corticotrophic releasing factor (crf), dynorphin, endorphin, fmlp and other formylated peptides, follitropin (fsh), fungal mating pheremones, galanin, gastric inhibitory polypeptide receptor (gip), glucagon-like peptides (glps), glucagon, gonadotropin releasing hormone (gnrh), growth hormone releasing hormone (ghrh), insect diuretic hormone, interleukin-8, leutropin (lh/hcg), met-enkephalin, opioid peptides, oxytocin, parathyroid hormone (pth) and pthrp, pituitary adenylyl cyclase activiating peptide (pacap), secretin, somatostatin, thrombin, thyrotropin (tsh), vasoactive intestinal peptide (vip), vasopressin, vasotocin; eicosanoids such as ip-prostacyclin, pg-prostaglandins, tx-thromboxanes; retinal based compounds such as vertebrate 11-cis retinal, invertebrate 11-cis retinal and other related compounds; lipids and lipid-based compounds such as cannabinoids, anandamide, lysophosphatidic acid, platelet activating factor, leukotrienes and the like; excitatory amino acids and ions such as calcium ions and glutamate.

Suitable examples of G-protein coupled receptors include, but are not limited to, dopaminergic, muscarinic cholinergic, α-adrenergic, β-adrenergic, opioid (including delta and mu), cannabinoid, serotoninergic, and GABAergic receptors. Preferred receptors include the 5HT family of receptors, dopamine receptors, C5a receptor and FPRL-1 receptor, cyclo-histidyl-proline-diketopiperazine receptors, melanocyte stimulating hormone release inhibiting factor receptor, and receptors for neurotensin, thyrotropin releasing hormone, calcitonin, cholecytokinin-A, neurokinin-2, histamine-3, cannabinoid, melanocortin, or adrenomodulin, neuropeptide-Yl or galanin. Other suitable receptors are listed in the art. The term "receptor," as used herein, encompasses both naturally occurring and mutant receptors.

Many of these G protein-coupled receptors, like the yeast a- and α-factor receptors, contain seven hydrophobic amino acid-rich regions which are assumed to lie within the plasma membrane. Specific human G protein-coupled STRs for which genes have been isolated and for which expression vectors could be constructed include those listed herein and others known in the art. Thus, the gene would be operably linked to a promoter functional in the cell to be engineered and to a signal sequence that also functions in the cell. For example in the case of yeast, suitable promoters include STE2, STE3 and GAL10. Suitable signal sequences include those of STE2, STE3 and of other genes which encode proteins secreted by yeast cells. Preferably, when a yeast cell is used, the codons of the gene would be optimized for expression in yeast. See Hoekema et al. (Mol. Cell. Biol. 7: 2914-24, 1987); Sharp, et al. (14: 5125-43, 1986).

The homology of STRs is discussed in Dohlman et al. (Ann. Rev. Biochem. 60: 653-88, 1991). When STRs are compared, a distinct spatial pattern of homology is discernible. The transmembrane domains are often the most similar, whereas the N- and C-terminal regions, and the cytoplasmic loop connecting transmembrane segments V and VI are more divergent.

The functional significance of different STR regions has been studied by introducing point mutations (both substitutions and deletions) and by constructing chimeras of different but related STRs. Synthetic peptides corresponding to individual segments have also been tested for activity. Affinity labeling has been used to identify ligand binding sites.

It is conceivable that when the host cell is a yeast cell, a foreign receptor will fail to functionally integrate into the yeast membrane, and there interact with the endogenous yeast G protein. More likely, either the receptor will need to be modified (e.g., by replacing its V-VI loop with that of the yeast STE2 or STE3 receptor), or a compatible G protein should be provided.

If the wild-type exogenous G protein-coupled receptor cannot be made functional in yeast, it may be mutated for this purpose. A comparison would be made of the amino acid sequences of the exogenous receptor and of the yeast receptors, and regions of high and low homology identified. Trial mutations would then be made to distinguish regions involved in ligand or G protein binding, from those necessary for functional integration in the membrane.

The exogenous receptor would then be mutated in the latter region to more closely resemble the yeast receptor, until functional integration was achieved. If this were insufficient to achieve functionality, mutations would next be made in the regions involved in G protein binding. Mutations would be made in regions involved in ligand binding only as a last resort, and then an effort would be made to preserve ligand binding by making conservative substitutions whenever possible.

In the case of an exogenous G-protein coupled receptor, the host cell must be able to produce a G protein which is activated by the exogenous receptor, and which can in turn activate the cell's effector(s). The art suggests that the endogenous host Gα subunit (e.g., GPA) will be often be sufficiently homologous to the "cognate" Gα subunit which is natively associated with the exogenous receptor for coupling to occur. In some instances, such as expression of mammalian receptors in yeast cells, it will be necessary to genetically engineer the host cell to produce a foreign Gα subunit which can properly interact with the exogenous receptor. For example, the Gα subunit of the yeast G protein may be replaced by the Gα subunit natively associated with the exogenous receptor.

Dietzel and Kurjan (Cell 50: 1001, 1987) demonstrated that rat Gαs functionally coupled to the yeast Gβγ complex. However, rat Gαi2 complemented only when substantially overexpressed, while Gαo did not complement at all. (Kang et al., Mol. Cell. Biol. 10: 2582, 1990). Consequently, with some foreign Gα subunits, it is not feasible to simply replace the yeast Gα.

If the exogenous G protein coupled receptor is not adequately coupled to yeast Gβγ by the Gα subunit natively associated with the receptor, the Gα subunit may be modified to improve coupling. These modifications often will take the form of mutations which increase the resemblance of the Gα subunit to the yeast Gα while decreasing its resemblance to the receptor-associated Gα. For example, a residue may be changed so as to become identical to the corresponding yeast Gα residue, or to at least belong to the same exchange group of that residue. After modification, the modified Gα subunit might or might not be "substantially homologous" to the foreign and/or the yeast Gα subunit.

The modifications are preferably concentrated in regions of the Gα which are likely to be involved in Gβγ binding. In some embodiments, the modifications will take the form of replacing one or more segments of the receptor-associated Gα with the corresponding yeast Gα segment(s), thereby forming a chimeric Gα subunit. (For the purpose of the appended claims, the term "segment" refers to three or more consecutive amino acids.) In other embodiments, point mutations may be sufficient.

This chimeric Gα subunit will interact with the exogenous receptor and the yeast Gβγ complex, thereby permitting signal transduction. While use of the endogenous yeast Gβγ is preferred, if a foreign or chimeric Gβγ is capable of transducing the signal to the yeast effector, it may be used instead.

Some aspects of Gα structure are relevant to the design of modified Gα subunits. The amino terminal 66 residues of GPA1 are aligned with the cognate domains of human Gαs, Gαi2, Gαi3, Gα16 and transducin. In the GPA41Gα hybrids, the amino terminal 41 residues (derived from GPA1) are identical, end with the sequence-LEKQRDKNE-(SEQ ID NO: 1) and are underlined for emphasis. All residues following the glutamate (E) residue at position 41 are contributed by the human Gα subunits, including the consensus nucleotide binding motif -GxGxxG-. Periods in the sequences indicate gaps that have been introduced to maximize alignments in this region. Codon bias is mammalian. For alignments of the entire coding regions of GPA1 with Gαs, Gαi, and Gαo, Gαq and Gαz, see Dietzel and Kurjan (Cell 50: 573, 1987) and Lambright et al. (Nature 369: 621-628, 1994). Additional sequence information is provided by Mattera et al. (FEBS Lett 206: 36-41, 1986), Bray et al. (Proc. Natl. Acad. Sci. USA 83: 8893-8897, 1986) and Bray et al. (Proc. Natl. Acad. Sci. USA 84: 5115-5119, 1987).

The gene encoding a G protein homolog of *S. cerevisiae* was cloned independently by Dietzel and Kurjan (supra) (SCG1) and by Nakafuku et al. (Proc. Natl. Acad. Sci. 84: 2140-2144, 1987) (GPA1). Sequence analysis revealed a high degree of homology between the protein encoded by this gene and mammalian Gα. GPA1 encodes a protein of 472 amino acids, as compared with approximately 340-350 a.a. for most mammalian Gα subunits in four described families, Gαs, Gαd, Gαq and Gα12/13. Nevertheless, GPA1 shares overall sequence and structural homology with all Gα proteins identified to date. The highest overall homology in GPA1 is to the Gαi family (48% identity, or 65% with conservative substitutions) and the lowest is to GQS (33% identity, or 51% with conservative substitutions) (Nakafuku et al., supra).

The regions of high sequence homology among Gα subunits are dispersed throughout their primary sequences, with the regions sharing the highest degree of homology mapping to sequence that comprises the guanine nucleotide binding/GTPase domain. This domain is structurally similar to the αβ fold of ras proteins and the protein synthesis elongation factor EF-Tu. This highly conserved guanine nucleotide-binding domain consists of a six-stranded β sheet surrounded by a set of five α-helices. It is within these β sheets and α helices that the highest degree of conservation is observed among all Gα proteins, including GPA1. The least sequence and structural homology is found in the intervening loops between the β sheets and α helices that define the core GTPase domain. There are a total of four "intervening loops" or "inserts" present in all Gα subunits. In the crystal structures reported to date for the GDP- and GTPγS-liganded forms of bovine rod transducin (Noel et al., Nature 366: 654-663, 1993); (Lambright et al., Nature 369: 621-628, 1994), the loop residues are found to be outside the core GTPase structure. Functional roles for these loop structures have been established in only a few instances. A direct role in coupling to phosphodiesterase-γ has been demonstrated for residues within inserts 3 and 4 of Gαt (Rarick et al., Science 256: 1031-1033, 1992); (Artemyev et al., J. Biol. Chem. 267: 25067-25072, 1992), while a "GAP-like" activity has been ascribed to the largely a-helical insert 1 domain of Gαs (Markby et al., Science 262: 1805-1901, 1993).

While the amino- and carboxy-termini of Gα subunits do not share striking homology either at the primary, secondary, or tertiary levels, there are several generalizations that can be made about them. First, the amino termini of Gα subunits have been implicated in the association of Gα with Gβγ complexes and in membrane association via N-terminal myristoylation. In addition, the carboxy-termini have been implicated in the association of Gαβγ heterotrimeric complexes with G protein-coupled receptors (Sullivan et al., Nature 330: 758-760, 1987; West et al., J. Biol. Chem. 260: 14428-14430, 1985; Conklin et al., Nature 363: 274-276, 1993). Data in support of these generalizations about the function of the N-terminus derive from several sources, including both biochemical and genetic studies.

As indicated above, there is little if any sequence homology shared among the amino termini of Gα subunits. The amino terminal domains of Gα subunits that precede the first β-sheet (containing the sequence motif -LLLLGAGESG- (SEQ ID NO: 2); see Noel et al., Supra, for the numbering of the structural elements of Gα subunits) vary in length from 41 amino acids (GPA1) to 31 amino acids (Gαt). Most Gα subunits share the consensus sequence for the addition of myristic acid at their amino termini (MGxxxS-), although not all Gα subunits that contain this motif have myristic acid covalently associated with the glycine at position 2 (Speigel et al., TIES 16: 338-3441, 1991). The role of this post-translational modification has been inferred from studies in which the activity of mutant Gα subunits from which the consensus sequence for myristoylation has been added or deleted has been assayed (Mumby et al., Proc. Natl. Acad. Sci. USA 87: 728-7321990; Linder et al., J. Biol Chem. 266: 4654-4659, 1991; Gallego et al., Proc. Natl. Acad. Sci. USA 89: 9695-9699, 1992). These studies suggest two roles for N-terminal myristoylation. First, the presence of amino-terminal myristic acid has in some cases been shown to be required for association of Gα subunits with the membrane, and second, this modification has been demonstrated to play a role in modulating the association of Gα subunits with Gβγ complexes. The role of myristoylation of the GPA1 gene products is, at present, unknown.

In other biochemical studies aimed at examining the role of the amino-terminus of Gα in driving the association between Gα and Gβγ subunits, proteolytically or genetically truncated versions of Gα subunits were assayed for their ability to associate with Gβγ complexes, bind guanine nucleotides and/ or to activate effector molecules. In all cases, Gα subunits with truncated amino termini were deficient in all three functions (Graf et al., J. Biol. Chem. 267: 24307-24314, 1992; Journot et al., J. Biol. Chem. 265: 9009-9015, 1990; and Neer et al., J. Biol. Chem 263: 8996-9000, 1988). Slepak et al. (J. Biol. Chem. 268: 1414-1423, 1993) reported a mutational analysis of the N-terminal 56 a.a. of mammalian Gαo expressed in *Escherichia coli*. Molecules with an apparent reduced ability to interact with exogenously added mammalian Gβγ were identified in the mutant library. As the authors pointed out, however, the assay used to screen the mutants the extent of ADP-ribosylation of the mutant Gα by pertussis toxin was not a completely satisfactory probe of interactions between Gα and Gβγ. Mutations identified as inhibiting the interaction of the subunits, using this assay, may still permit the complexing of Gα and Gβγ while sterically hindering the ribosylation of Gα by toxin. Genetic studies examined the role of amino-terminal determinants of Gα in heterotrimer subunit association have been carried out in both yeast systems using GPA1-mammalian Gα hybrids (Kang et al., Mol. Cell. Biol. 10: 2582-2590, 1990) and in mammalian systems using Gαi/Gαs hybrids (Russell and Johnson, Mol. Pharmacol. 44: 255-263, 1993). In the former studies, gene fusions, composed of yeast GPA1 and mammalian Gα sequences were constructed by Kang, et al. (supra) and assayed for their ability to complement a gpal null phenotype (i.e., constitutive activation of the pheromone response pathway) in *S. cerevisiae*. Kang, et al. demonstrated that wild type mammalian Gαs, Gαi but not Gαo proteins are competent to associate with yeast Gα and suppress the gpal null phenotype, but only when overexpressed. Fusion proteins containing the amino-terminal 330 residues of GPA1 sequence linked to 160, 143, or 142 residues of the mammalian Gαs, Gαd and Gαo carboxyl-terminal regions, respectively, also coupled to the yeast mating response pathway when overexpressed on high copy plasmids with strong inducible (CUP) or constitutive (PGK) promoters. All three of these hybrid molecules were able to complement the gpal null mutation in a growth arrest assay, and were additionally able to inhibit a factor responsiveness and mating in tester strains. These last two observations argue that hybrid yeast-mammalian Gα subunits are capable of interacting directly with yeast Gβγ, thereby disrupting the normal function of the yeast heterotrimer. Fusions containing the amino terminal domain of Gαs, Gαi or Gαo, however, did not complement the gpal null phenotype, indicating a requirement for determinants in the amino terminal 330 amino acid residues of GPA1 for association and sequestration of yeast Gβγ complexes. Taken together, these data suggest that determinants in the amino terminal region of Gα subunits determine not only the ability to associate with Gβγ subunits in general, but also with specific Gβγ subunits in a species-restricted manner.

Hybrid Gαi/Gαs subunits have been assayed in mammalian expression systems. (Russell and Johnson, supra). In these studies, a large number of chimeric Gα subunits were assayed for an ability to activate adenylyl cyclase, and therefore, indirectly, for an ability to interact with Gβγ (i.e., coupling of Gα to Gβγ=inactive cyclase; uncoupling of Gα from Gβγ=active cyclase). From these studies a complex picture emerged in which determinants in the region between residues 25 and 96 of the hybrids were found to determine the state of activation of these alleles as reflected in their rates of guanine nucleotide exchange and GTP hydrolysis and the extent to which they activated adenylyl cyclase in vivo. These data could be interpreted to support the hypothesis that structural elements in the region between the amino terminal methionine and the ~1 sheet identified in the crystal structure of Gαt (see Noel et al., supra and Lambright et al., supra) are involved in determining the state of activity of the heterotrimer by (1) driving association/dissociation between Gα and Gβγ subunits; (2) driving GDP/GTP exchange. While there is no direct evidence provided by these studies to support the idea that residues in this region of Gα and residues in Gβγ subunits contact one another, the data nonetheless provide a positive indication for the construction of hybrid Gα subunits that retain function. There is, however, a negative indicator that derives from this work in that some hybrid constructs resulted in constitutive activation of the chimeric proteins (i.e., a loss of receptor-dependent stimulation of Gβγ dissociation and effector activation).

In designing Gα subunits capable of transmitting, in yeast, signals originating at mammalian G protein-coupled receptors, two general desiderata were recognized. First, the subunits should retain as much of the sequence of the native mammalian proteins as possible. Second, the level of expression for the heterologous components should approach, as closely as possible, the level of their endogenous counterparts. The results described by King et al. (Science 250: 121-123, 1990) for expression of the human (32-adrenergic receptor and Gαs in yeast, taken together with negative results obtained by Kang et al. (supra) with full-length mammalian Gα subunits other than Gαs, led us to the following preferences for the development of yeast strains in which mammalian G protein-coupled receptors could be linked to the pheromone response pathway.

1. Mammalian Gα subunits will be expressed using the native sequence of each subunit or, alternatively, as minimal gene fusions with sequences from the amino- terminus of GPA1 replacing the homologous residues from the mammalian Gα subunits.

2. Mammalian Gα subunits will be expressed from the GPA1 promoter either on low copy plasmids or after integration into the yeast genome as a single copy gene.

3. Endogenous Gβγ subunits will be provided by the yeast STE4 and STE18 loci.

An alternative to the modification of a mammalian Gα subunit for improved signal transduction is the modification of the pertinent sites in the yeast Gβ or Gγ subunits. The principles discussed already with respect to Gα subunits apply, mutatis mutandis, to yeast Gβ or Gγ.

For example, it would not be unreasonable to target the yeast Ste4p Gβ subunit with cassette mutagenesis. Specifically, the region of Ste4p that encodes several of the dominant negative, signaling-defective mutations would be an excellent target for cassette mutagenesis when looking for coupling of yeast Gβγ to specific mammalian Gα subunits.

E. Cytokine Receptors

In another embodiment the target receptor is a cytokine receptor. Cytokines are a family of soluble mediators of cell-to-cell communication that includes interleukins, interferons, and colony-stimulating factors. The characteristic features of cytokines lie in their functional redundancy and pleiotropy. Most of the cytokine receptors that constitute distinct superfamilies do not possess intrinsic protein tyrosine kinase domains, yet receptor stimulation usually invokes rapid tyrosine phosphorylation of intracellular proteins, including the receptors themselves. Many members of the cytokine receptor superfamily activate the JAK protein tyrosine kinase family, with resultant phosphorylation of the STAT transcriptional activator factors. IL-2, IL-7, IL-2 and Interferon γ have all been shown to activate JAK kinases (Frank et al., Proc. Natl. Acad. Sci. USA 92: 7779-7783, 1995; Scharfe et al., Blood 86: 2077-2085, 1995; Bacon et al., Proc. Natl. Acad. Sci. USA 92: 7307-7311, 1995; and Sakatsume et al., J. Biol Chem 270: 17528-17534, 1995). Events downstream of JAK phosphorylation have also been elucidated. For example, exposure of T lymphocytes to IL-2 has been shown to lead to the phosphorylation of signal transducers and activators of transcription (STAT) proteins STAT1α, STAT2β, and STAT3, as well as of two STAT-related proteins, p94 and p95. The STAT proteins were found to translocate to the nucleus and to bind to a specific DNA sequence, thus suggesting a mechanism by which IL-2 may activate specific genes involved in immune cell function (Frank et al., supra). Jak3 is associated with the gamma chain of the IL-2, IL-4, and IL-7 cytokine receptors (Fujii et al., Proc. Natl. Acad. Sci. 92: 5482-5486, 1995 and Musso et al., J. Exp. Med. 181: 1425-1431, 1995). The JAK kinases have also been shown to be activated by numerous ligands that signal via cytokine receptors such as, growth hormone and erythropoietin and IL-6 (Kishimoto, Stem cells Suppl 12: 37-44, 1994).

Detection means which may be scored for in the present assay, in addition to direct detection of second messengers, such as by changes in phosphorylation, includes reporter constructs or indicator genes which include transcriptional regulatory elements responsive to the STAT proteins. Described infra.

F. Multisubunit Immune Recognition Receptor (MIRR).

In still another embodiment the receptor is a multisubunit receptor. Receptors can be comprised of multiple proteins referred to as subunits, one category of which is referred to as a multisubunit receptor is a multisubunit immune recognition receptor (MIRR). MIRRs include receptors having multiple noncovalently associated subunits and are capable of interacting with src-family tyrosine kinases. MIRRs can include, but are not limited to, B cell antigen receptors, T cell antigen receptors, Fc receptors and CD22. One example of an MIRR is an antigen receptor on the surface of a B cell. To further illustrate, the MIRR on the surface of a B cell comprises membrane-bound immunoglobulin (mIg) associated with the subunits Ig-α and Ig-β or Ig-γ, which forms a complex capable of regulating B cell function when bound by antigen. An antigen receptor can be functionally linked to an amplifier molecule in a manner such that the amplifier molecule is capable of regulating gene transcription.

Src-family tyrosine kinases are enzymes capable of phosphorylating tyrosine residues of a target molecule. Typically, a src-family tyrosine kinase contains one or more binding domains and a kinase domain. A binding domain of a src-family tyrosine kinase is capable of binding to a target molecule and a kinase domain is capable of phosphorylating a target molecule bound to the kinase. Members of the src family of tyrosine kinases are characterized by an N-terminal unique region followed by three regions that contain different degrees of homology among all the members of the family. These three regions are referred to as src homology region 1 (SH1), src homology region 2 (SH2) and src homology region 3 (SH3). Both the SH2 and SH3 domains are believed to have protein association functions important for the formation of signal transduction complexes. The amino acid sequence of an N-terminal unique region, varies between each src-family tyrosine kinase. An N-terminal unique region can be at least about the first 40 amino acid residues of the N-terminal of a src-family tyrosine kinase.

Syk-family kinases are enzymes capable of phosphorylating tyrosine residues of a target molecule. Typically, a syk-family kinase contains one or more binding domains and a kinase domain. A binding domain of a syk-family tyrosine kinase is capable of binding to a target molecule and a kinase domain is capable of phosphorylating a target molecule bound to the kinase. Members of the syk- family of tyrosine kinases are characterized by two SH2 domains for protein association function and a tyrosine kinase domain.

A primary target molecule is capable of further extending a signal transduction pathway by modifying a second messenger molecule. Primary target molecules can include, but are not limited to, phosphatidylinositol 3-kinase (PI-3K), P21 rasGAPase-activating protein and associated p190 and p62 protein, phospholipases such as PLCγ1 and PLCγ2, MAP kinase, Shc and VAV. A primary target molecule is capable of producing second messenger molecule which is capable of further amplifying a transduced signal. Second messenger molecules include, but are not limited to diacylglycerol and inositol 1,4,5-triphosphate (IP3). Second messenger molecules are capable of initiating physiological events which can lead to alterations in gene transcription. For example, production of IP3 can result in release of intracellular calcium, which can then lead to activation of calmodulin kinase 11, which can then lead to serine phosphorylation of a DNA binding protein referred to as ETS-1 proto-onco-protein. Diacylglycerol is capable of activating the signal transduction protein, protein kinase C which affects the activity of the AP1

DNA binding protein complex. Signal transduction pathways can lead to transcriptional activation of genes such as c-fos, egr-1, and c-myc.

Shc can be thought of as an adapter molecule. An adapter molecule comprises a protein that enables two other proteins to form a complex (e.g., a three molecule complex). Shc protein enables a complex to form which includes Grb2 and SOS. Shc comprises an SH2 domain that incapable of associating with the SH2 domain of Grb2.

Molecules of a signal transduction pathway can associate with one another using recognition sequences. Recognition sequences enable specific binding between two molecules. Recognition sequences can vary depending upon the structure of the molecules that are associating with one another. A molecule can have one or more recognition sequences, and as such can associate with one or more different molecules.

Signal transduction pathways for MIRR complexes are capable of regulating the biological functions of a cell. Such functions can include, but are not limited to the ability of a cell to grow, to differentiate and to secrete cellular products. MIRR-induced signal transduction pathways can regulate the biological functions of specific types of cells involved in particular responses by an animal, such as immune responses, inflammatory responses and allergic responses. Cells involved in an immune response can include, for example, B cells, T cells, macrophages, dendritic cells, natural killer cells and plasma cells. Cells involved in inflammatory responses can include, for example, basophils, mast cells, eosinophils, neutrophils and macrophages. Cells involved in allergic responses can include, for example mast cells, basophils, B cells, T cells and macrophages.

In exemplary embodiments of the subject assay, the detection signal is a second messengers, such as a phosphorylated src-like protein, includes reporter constructs or indicator genes which include transcriptional regulatory elements such as serum response element (SRE), 12-O-tetradecanoyl-phorbol-13-acetate response element, cyclic AMP response element, c-fos promoter, or a CREB-responsive element.

G. Receptor Tyrosine Kinases.

In yet another embodiment, the target receptor is a receptor tyrosine kinase. The receptor tyrosine kinases can be divided into five subgroups on the basis of structural similarities in their extracellular domains and the organization of the tyrosine kinase catalytic region in their cytoplasmic domains. Sub-groups I (epidermal growth factor (EGF) receptor-like), II (insulin receptor-like) and the eph/eck family contain cysteine-rich sequences (Hirai et al., Science 238: 1717-1720, 1987 and Lindberg and Hunter, Mol. Cell. Biol. 10: 6316-6324, 1990).The functional domains of the kinase region of these three classes of receptor tyrosine kinases are encoded as a contiguous sequence (Hanks et al., Science 241: 42-52, 1988). Subgroups III (platelet-derived growth factor (PDGF) receptor-like) and IV (the fibro-blast growth factor (FGF) receptors) are characterized as having immunoglobulin (Ig)-like folds in their extracellular domains, as well as having their kinase domains divided in two parts by a variable stretch of unrelated amino acids (Yanden and Ullrich, 1988, supra and Hanks et al., 1988, supra).

The family with by far the largest number of known members is the EPH family. Since the description of the prototype, the EPH receptor (Hirai et al., Science 238: 1717-1720, 1987), sequences have been reported for at least ten members of this family, not counting apparently orthologous receptors found in more than one species. Additional partial sequences, and the rate at which new members are still being reported, suggest the family is even larger (Maisonpierre et al., Oncogene 8: 3277-3288, 1993; Andres et al., Oncogene 9: 1461-1467, 1994; Henkemeyer et al., Oncogene 9: 1001-1014, 1994; Ruiz et al., Mech Dev 46: 87-100, 1994; Xu et al., Development 120: 287-299, 1994; Zhou et al., J Neurosci Res 37: 129-143, 1994; and references in Tuzi and Gullick, Br J Cancer 69: 417-421, 1994). Remarkably, despite the large number of members in the EPH family, all of these molecules were identified as orphan receptors without known ligands.

The expression patterns determined for some of the EPH family receptors have implied important roles for these molecules in early vertebrate development. In particular, the timing and pattern of expression of sek, mek4 and some of the other receptors during the phase of gastrulation and early organogenesis has suggested functions for these receptors in the important cellular interactions involved in patterning the embryo at this stage (Gilardi-Hebenstreit et al., Oncogene 7: 2499-2506, 1992; Nieto et al., Development 116: 1137-1150, 1992; Henkemeyer et al., supra; Ruiz et al., supra; and Xu et al., supra). Sek, for example, shows a notable early expression in the two areas of the mouse embryo that show obvious segmentation, namely the somites in the mesoderm and the rhombomeres of the hindbrain; hence the name sek, for segmentally expressed kinase (Gilardi-Hebenstreit et al., supra; Nieto et al., supra). As in *Drosophila,* these segmental structures of the mammalian embryo are implicated as important elements in establishing the body plan. The observation that Sek expression precedes the appearance of morphological segmentation suggests a role for sek in forming these segmental structures, or in determining segment-specific cell properties such as lineage compartmentation (Nieto et al., supra). Moreover, EPH receptors have been implicated, by their pattern of expression, in the development and maintenance of nearly every tissue in the embryonic and adult body. For instance, EPH receptors have been detected throughout the nervous system, the testes, the cartilaginous model of the skeleton, tooth primordia, the infundibular component of the pituitary, various epithelia tissues, lung, pancreas, liver and kidney tissues. Observations such as this have been indicative of important and unique roles for EPH family kinases in development and physiology, but further progress in understanding their action has been severely limited by the lack of information on their ligands.

As used herein, the terns "EPH receptor" or "EPH-type receptor" refer to a class of receptor tyrosine kinases, comprising at least eleven paralogous genes, though many more orthologs exist within this class, e.g. homologs from different species. EPH receptors, in general, are a discrete group of receptors related by homology and easily recognizable, e.g., they are typically characterized by an extracellular domain containing a characteristic spacing of cysteine residues near the N-terminus and two fibronectin type III repeats (Hirai et al., Science 238: 1717-1720, 1987; Lindberg et al., Mol Cell Biol 10: 6316-6324, 1990; Chan et al., Oncogene 6: 1057-1061, 1991; Maisonpierre et al., Oncogene 8: 3277-3288, 1993; Andres et al., Oncogene 9: 1461-1467, 1994; Henkemeyer et al., Oncogene 9: 1001-1014, 1994; Ruiz et al., Mech Dev 46: 87-100, 1994; Xu et al., Development 120: 287-299, 1994; Zhou et al., J. Neurosci Res 37: 129-143, 1994; and references in Tuzi and Gullick, Br J Cancer 69: 417-421, 1994). Exemplary EPH receptors include the eph, elk, eck, sek, mek4, hek, hek1, eek, erk, tyro1, tyro4, tyros, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. The term "EPH receptor" refers to the membrane form of the receptor protein, as well as fragments which retain the ability to activate the receptor pathway.

In exemplary embodiments, the detection signal is provided by detecting phosphorylation of intracellular proteins, e.g., MEKKs, MEKs, or Map kinases, or by the use of reporter constructs or indicator genes which include transcriptional regulatory elements responsive to c-fos and/or c-jun. Described infra.

H. Screening and Selection of Activating Mutants

When screening for activating mutations, intracellular second messenger generation can be measured directly. A variety of intracellular effectors have been identified as being receptor-or ion channel-regulated, including adenylyl cyclase, cyclic GMP, phosphodiesterases, phosphoinositidases, phosphoinositol kinases, and phospholipases, as well as a variety of ions.

In one embodiment, the GTPase enzymatic activity by G proteins can be measured in plasma membrane preparations by determining the breakdown of $\gamma^{32}P$ GTP using techniques that are known in the art (For example, see Signal Transduction: A Practical Approach. G. Milligan, Ed. Oxford University Press, Oxford England). When receptors that modulate cAMP are tested, it will be possible to use standard techniques for cAMP detection, such as competitive assays which quantitate [$^3$H] cAMP in the presence of unlabelled cAMP.

Certain receptors and ion channels stimulate the activity of phospholipase C which stimulates the breakdown of phosphatidylinositol 4,5, bisphosphate to 1,4,5-IP3 (which mobilizes intracellular $Ca^{++}$) and diacylglycerol (DAG) (which activates protein kinase C). Inositol lipids can be extracted and analyzed using standard lipid extraction techniques. DAG can also be measured using thin-layer chromatography. Water soluble derivatives of all three inositol lipids (IP1, IP2, IP3) can also be quantitated using radiolabelling techniques or HPLC.

The other product of $PIP_2$ breakdown, DAG can also be produced from phosphatidyl choline. The breakdown of this phospholipid in response to receptor-mediated signaling can also be measured using a variety of radiolabelling techniques.

The activation of phospholipase A2 can easily be quantitated using known techniques, including, for example, the generation of arachadonate in the cell.

In various cells, e.g., mammalian cells, specific proteases are induced or activated in each of several arms of divergent signaling pathways. These may be independently monitored by following their unique activities with substrates specific for each protease.

In the case of certain receptors and ion channels, it may be desirable to screen for changes in cellular phosphorylation. Such assay formats may be useful when the receptor of interest is a receptor kinase or phosphatase. For example, immunoblotting (Lyons and Nelson, Proc. Natl. Acad. Sci. USA 81: 7426-7430, 1984) using anti-phosphotyrosine, anti-phosphoserine or anti-phosphothreonine antibodies. In addition, tests for phosphorylation could be also useful when the receptor itself may not be a kinase, but activates protein kinases or phosphatase that function downstream in the signal transduction pathway.

One such cascade is the MAP kinase pathway that appears to mediate both mitogenic, differentiation and stress responses in different cell types. Stimulation of growth factor receptors results in Ras activation followed by the sequential activation of c-Raf, MEK, and p44 and p42 MAP kinases (ERK1 and ERK2). Activated MAP kinase then phosphorylates many key regulatory proteins, including p90RSK and Elk-1 that are phosphorylated when MAP kinase translocates to the nucleus. Homologous pathways exist in mammalian and yeast cells. For instance, an essential part of the *S. cerevisiae* pheromone signaling pathway is comprised of a protein kinase cascade composed of the products of the STE11, STE7, and FUS3/KSS1 genes (the latter pair are distinct and functionally redundant). Accordingly, phosphorylation and/or activation of members of this kinase cascade can be detected and. used to quantitate receptor engagement. Phosphotyrosine specific antibodies are available to measure increases in tyrosine phosphorylation and phospho-specific antibodies are commercially available (New England Biolabs, Beverly, Mass.).

In the case of certain receptors and ion channels, it may also be desirable to screen for changes in other post-translational modifications, including, but are not limited to, methylation, acetylation, prenylation, myristoylation, palmitoylation, glycosylation, ubiquitination etc., or any combination thereof. The assay of these modifications, including gel electrophoresis and chromatograpgy, are well-known in the art and thus will not be discussed further.

In yet another embodiment, the signal transduction pathway of the targeted receptor or ion channel upregulates expression or otherwise activates an enzyme that modifies a substrate which can be added to the cell. The signal can be detected by using a detectable substrate, in which case lose of the substrate signal is monitored, or alternatively, by using a substrate which produces a detectable product. In preferred embodiments, the conversion of the substrate to product by the activated enzyme produces a detectable change in optical characteristics of the test cell, e.g., the substrate and/or product is chromogenically or fluorogenically active. In an illustrative embodiment the signal transduction pathway causes a change in the activity of a proteolytic enzyme, altering the rate at which it cleaves a substrate peptide (or simply activates the enzyme towards the substrate). The peptide includes a fluorogenic donor radical, e.g., a fluorescence emitting radical, and an acceptor radical, e.g., an aromatic radical which absorbs the fluorescence energy of the fluorogenic donor radical when the acceptor radical and the fluorogenic donor radical are covalently held in close proximity. See, for example, U.S. Pat. Nos. 5,527,681, 5,506,115, 5,429,766, 5,424,186, and 5,316,691; and Capobianco et al., Anal Biochem 204: 96-102, 1992. For example, the substrate peptide has a fluorescence donor group such as 1-aminobenzoic acid (anthranilic acid or ABZ) or aminomethylcoumarin (AMC) located at one position on the peptide and a fluorescence quencher group, such as lucifer yellow, methyl red or nitrobenzo-2-oxo-1,3-diazole (NBD), at a different position near the distal end of the peptide. A cleavage site for the activated enzyme will be diposed between each of the sites for the donor and acceptor groups. The intramolecular resonance energy transfer from the fluorescence donor molecule to the quencher will quench the fluorescence of the donor molecule when the two are sufficiently proximate in space, e.g., when the peptide is intact. Upon cleavage of the peptide, however, the quencher is separated from the donor group, leaving behind a fluorescent fragment. Thus, activation of the enzyme results in cleavage of the detection peptide, and dequenching of the fluorescent group.

In a preferred embodiment, the enzyme which cleaves the detection peptide is one which is endogenous to the host cell. For example, the bar1 gene of yeast encodes a protease, the expression of which is upregulated by stimulation of the yeast pheromone pathway. Thus, host-cells which have been generated to exploit the pheromone signal pathway for detection can be contacted with a suitable detection peptide which can be cleaved by bar1 to release a fluorogenic fragment, and the level of bar1 activity thus determined.

In still other embodiments, the detectable signal can be produced by use of enzymes or chromogenic/fluorescent probes whose activities are dependent on the concentration of a second messenger, e.g., such as calcium, hydrolysis products of inositol phosphate, cAMP, etc. For example, the mobilization of intracellular calcium or the influx of calcium from outside the cell can be measured using standard techniques. The choice of the appropriate calcium indicator, fluorescent, bioluminescent, metallochromic, or $Ca^{++}$-sensitive microelectrodes depends on the cell type and the magnitude and time constant of the event under study (Borle, Environ Health Perspect. 84: 45-56, 1990). As an exemplary method of $Ca^{++}$ detection, cells could be loaded with the $Ca^{++}$ sensitive fluorescent dye fura-2 or indo-1, using standard methods, and any change in $Ca^{++}$ measured using a fluorometer.

As certain embodiments described above suggest, in addition to directly measuring second messenger production, the signal transduction activity of a receptor or ion channel pathway can be measured by detection of a transcription product, e.g., by detecting receptor/channel-mediated transcriptional activation (or repression) of a gene(s). Detection of the transcription product includes detecting the gene transcript, detecting the product directly (e.g., by immunoassay) or detecting an activity of the protein (e.g., such as an enzymatic activity or chromogenic/fluorogenic activity); each of which is generally referred to herein as a means for detecting expression of the indicator gene. The indicator gene may be an unmodified endogenous gene of the host cell, a modified endogenous gene, or a part of a completely heterologous construct, e.g., as part of a reporter gene construct.

In one embodiment, the indicator gene is an unmodified endogenous gene. For example, the instant method can rely on detecting the transcriptional level of such endogenous genes as the c-fos gene (e.g., in mammalian cells) or the Bar1 or Fus1 genes (e.g., in yeast cells) in response to such signal transduction pathways as originating from G protein coupled receptors.

In certain instances, it may be desirable to increase the level of transcriptional activation of the endogenous indicator gene by the signal pathway in order to, for example, improve the signal-to-noise of the test system, or to adjust the level of response to a level suitable for a particular detection technique. In one embodiment, the transcriptional activation ability of the signal pathway can be amplified by the overexpression of one or more of the proteins involved in the intracellular signal cascade, particularly enzymes involved in the pathway. For example, increased expression of Jun kinases (JNKs) can potentiate the level of transcriptional activation by a signal in an MEKK/JNKK pathway. Likewise, overexpression of one or more signal transduction proteins in the yeast pheromone pathway can increase the level of Fus1 and/or Bar1 expression. This approach can, of course, also be used to potentiate the level of transcription of a heterologous reporter gene as well.

In other embodiments, the sensitivity of an endogenous indicator gene can be enhanced by manipulating the promoter sequence at the natural locus for the indicator gene. Such manipulation may range from point mutations to the endogenous regulatory elements to gross replacement of all or substantial portions of the regulatory elements. In general, manipulation of the genomic sequence for the indicator gene can be carried out using techniques known in the art, including homologous recombination.

In an exemplary embodiment, the yeast bar1 promoter can be engineered by mutagenesis to be more responsive, e.g., to more strongly promoter gene transcription, upon stimulation of the yeast pheromone pathway. Thus, the endogenous bar1 promoter of a yeast cell can be replaced, e.g., by homologous recombination, with a bar1 promoter engineered to cause higher levels of expression of bar1 upon pheromone stimulation, and the level of bar1 can be detected, for example, by use of a fluorogenic substrate as described above.

In another exemplary embodiment, the promoter (or other transcriptional regulatory sequences) of the endogenous gene can be "switched out" with a heterologous promoter sequence, e.g., to form a chimeric gene at the indicator gene locus. Again, using such techniques as homologous recombination, the regulatory sequence can be so altered at the genomic locus of the indicator gene. For example, the bar1 promoter can be replaced, at the bar1 locus, with the promoter for the fus1 gene. The fus1 promoter has a higher responsiveness to stimulation by pheromone induction than the bar1 promoter, accordingly can increase the signal-to-noise and dynamic range of the indicator gene. For other exemplary embodiments, we note that we have substituted the fus1 and fus2 promoters at other loci, such as for the can1 promoter. These strains will become canavanine sensitive upon expression of the can1 gene. A similar approach was used to introduce the fus1 and fus2 promoter upstream of the ura3 gene in place of the ura3 promoter, thus conferring uracil prototrophy in a manner dependent on activation of the yeast pheromone signal pathway. Likewise, the fus1 and fus2 promoter regions can be introduced upstream of such genes in order to control their expression: gall (conferring deoxygalactose sensitivity or galactose sensitivity due to the concomitant loss of the Ga110 gene); β-D-glucanase (exg1: an easily assayed extracellular enzyme); chitinase (cts1); asparaginase (ast3: hydrolyzes asparagine to ammonia and aspartate); and invertase (suc2); secreted acid phosphatase (pho3 or pho5).

In still another embodiment, a heterologous reporter gene construct can be used to provide the function of an indicator gene. Reporter gene constructs are prepared by operatively linking a reporter gene with at least one transcriptional regulatory element. If only one transcriptional regulatory element is included it must be a regulatable promoter. At least one of the selected transcriptional regulatory elements must be indirectly or directly regulated by the activity of the selected cell-surface receptor whereby activity of the receptor can be monitored via transcription of the reporter genes.

Many reporter genes and transcriptional regulatory elements are known to those of skill in the art and others may be identified or synthesized by methods known to those of skill in the art.

Examples of reporter genes include, but are not limited to CAT (chloramphenicol acetyl transferase) (Alton and Vapnek, Nature 282: 864-869, 1979) luciferase, and other enzyme detection systems, such as beta-Galactosidase; firefly luciferase (deWet et al., Mol. Cell. Biol. 7: 725-737, (1987); bacterial luciferase (Engebrecht and Silverman, PNAS 1: 4154-4158, 1984; Baldwin et al., Biochemistry 23: 3663-3667, 1984); alkaline phosphatase (Toh et al., Eur. J. Biochem. 182: 231-238, 1989, Hall et al., J. Mol. Appl. Gen. 2: 101, 1983), human placental secreted alkaline phosphatase (Cullen and Malim, Methods in Enzymol. 216: 362-368, 1992); β-lactamase or GST.

Transcriptional control elements for use in the reporter gene constructs, or for modifying the genomic locus of an indicator gene include, but are not limited to, promoters, enhancers, and repressor and activator binding sites. Suitable transcriptional regulatory elements may be derived from the transcriptional regulatory regions of genes whose expression is rapidly induced, generally within minutes, of contact between the cell surface protein and the effector protein that modulates the activity of the cell surface protein. Examples of such genes include, but are not limited to, the immediate early genes (see, Sheng et al., Neuron 4: 477-485, 1990), such as c-fos. Immediate early genes are genes that are rapidly induced upon binding of a ligand to a cell surface protein. The transcriptional control elements that are preferred for use in the gene constructs include transcriptional control elements from immediate early genes, elements derived from other genes that exhibit some or all of the characteristics of the immediate early genes, or synthetic elements that are constructed such that genes in operative linkage therewith exhibit such characteristics. The characteristics of preferred genes from which the transcriptional control elements are derived include, but are not limited to, low or undetectable expression in quiescent cells, rapid induction at the transcriptional level within minutes of extracellular simulation, induction that is transient and independent of new protein synthesis, subsequent shut-off of transcription requires new protein synthesis, and mRNAs transcribed from these genes have a short half-life. It is not necessary for all of these properties to be present.

Other promoters and transcriptional control elements, in addition to those described above, include the vasoactive intestinal peptide (VIP) gene promoter (cAMP responsive; Fink et al., Proc. Natl. Acad. Sci. 85: 6662-6666, 1988); the somatostatin gene promoter (cAMP responsive; Montminy et al., Proc. Natl. Acad. Sci. 83: 6682-6686, 1986; the proenkephalin promoter (responsive to cAMP, nicotinic agonists, and phorbol esters; Comb et al., Nature 323: 353-356, 1986); the phosphoenolpyruvate carboxy-kinase gene promoter (cAMP responsive; Short et al., J. Biol. Chem. 261: 9721-9726, 1986); the NGFI-A gene promoter (responsive to NGF, cAMP, and serum; Changelian et al., Proc. Natl. Acad. Sci. 86: 377-381, 1989); and others that maybe known to or prepared by those of skill in the art.

In the case of receptors which modulate cyclic AMP, a transcriptional based readout can be constructed using the cyclic AMP response element binding protein, CREB, which is a transcription factor whose activity is regulated by phosphorylation at a particular serine (S133). When this serine residue is phosphorylated, CREB binds to a recognition sequence known as a CRE (CAMP Responsive Element) found to the 5' of promoters known to be responsive to elevated cAMP levels. Upon binding of phosphorylated CREB to a CRE, transcription from this promoter is increased.

Phosphorylation of CREB is seen in response to both increased CAMP levels and increased intracellular Ca levels. Increased cAMP levels result in activation of PKA, which in turn phosphorylates CREB and leads to binding to CRE and transcriptional activation. Increased intracellular calcium levels results in activation of calcium/calmodulin responsive kinase II (CaM kinase II). Phosphorylation of CREB by CaM kinase II is effectively the same as phosphorylation of CREB by PKA, and results in transcriptional activation of CRE containing promoters.

Therefore, a transcriptionally-based readout can be constructed in cells containing a reporter gene whose expression is driven by a basal promoter containing one or more CRE. Changes in the intracellular concentration of $Ca^{++}$ (a result of alterations in the activity of the receptor upon engagement with a ligand) will result in changes in the level of expression of the reporter gene if: a) CREB is also co-expressed in the cell, and b) either an endogenous or heterologous CaM kinase phosphorylates CREB in response to increases in calcium or if an exogenously expressed CaM kinase II is present in the same cell. In other words, stimulation of PLC activity may result in phosphorylation of CREB and increased transcription from the CRE-construct, while inhibition of PLC activity may result in decreased transcription from the CRE-responsive construct.

As described in Bonni et al. (Science 262: 1575-1579, 1993), the observation that CNTF treatment of SK-N-MC cells leads to the enhanced interaction of STAT/p91 and STAT related proteins with specific DNA sequences suggested that these proteins might be key regulators of changes in gene expression that are triggered by CNTF. Consistent with this possibility is the finding that DNA sequence elements similar to the consensus DNA sequence required for STAT/p91 binding are present upstream of a number of genes previously found to be induced by CNTF (e.g., Human c-fos, Mouse c-fos, Mouse tis11, Rat junb, Rat SOD-1, and CNTF). Those authors demonstrated the ability of STAT/p91 binding sites to confer CNTF responsiveness to a non-responsive reporter gene. Accordingly, a reporter construct for use in the present invention for detecting signal transduction through STAT proteins, such as from cytokine receptors, can be generated by using −71 to +109 of the mouse c-fos gene fused to the bacterial chloramphenicol acetyltransferase gene (−71fos-CAT) or other detectable marker gene. Induction by a cytokine receptor induces the tyrosine phosphorylation of STAT and STAT-related proteins, with subsequent translocation and binding of these proteins to the STAT-RE. This then leads to activation of transcription of genes containing this DNA element within their promoters.

In preferred embodiments, the reporter gene is a gene whose expression causes a phenotypic change which is screenable or selectable. If the change is selectable, the phenotypic change creates a difference in the growth or survival rate between cells which express the reporter gene and those which do not. If the change is screenable, the phenotype change creates a difference in some detectable characteristic of the cells, by which the cells which express the marker may be distinguished from those which do not. Selection is preferable to screening in that it can provide a means for amplifying from the cell culture those cells which express an activated receptor or ion channel.

The marker gene is coupled to the receptor signaling pathway so that expression of the marker gene is dependent on activation of the receptor. This coupling may be achieved by operably linking the marker gene to a receptor-responsive promoter. The term "receptor-responsive promoter" indicates a promoter which is regulated by some product of the target receptor's signal transduction pathway.

Alternatively, the promoter may be one which is repressed by the receptor pathway, thereby preventing expression of a product which is deleterious to the cell. With a receptor repressed promoter, one screens for activated receptors by linking the promoter to a deleterious gene, and for antagonists, by linking it to a beneficial gene. Repression may be achieved by operably linking a receptor-induced promoter to a gene encoding mRNA which is antisense to at least a portion of the mRNA encoded by the marker gene (whether in the coding or flanking regions), so as to inhibit translation of that mRNA. Repression may also be obtained by linking a receptor-induced promoter to a gene encoding a DNA binding repressor protein, and incorporating a suitable operator site into the promoter or other suitable region of the marker gene.

In the case of yeast, suitable positively selectable (beneficial) genes include the following: URA3, LYS2, HIS3, LEU2, TRP, ADE1, 2, 3, 4, 5, 7, 8; ARGI, 3, 4, 5, 6, 8; HIS 1, 4, 5; ILV1, 2, 5; THR1, 4; TRP2, 3,4,5; LEU1, 4; MET2, 3, 4, 8, 9, 14, 16, 19; URA1, 2, 4, 5,10; HOM3, 6; ASP3; CHO1; ARO 2, 7; CYS3; OLE1; INO1, 2, 4; PRO1, 3. Countless other genes are potential selective markers. The above are involved in well-characterized biosynthetic pathways. The imidazoleglycerol phosphate dehydratase (IGP dehydratase) gene HIS3 is preferred because it is both quite sensitive and can be selected over a broad range of expression levels. In the simplest case, the cell is auxotrophic for histidine (requires histidine for growth) in the absence of activation. Activation leads to synthesis of the enzyme and the cell becomes prototrophic for histidine (does not require histidine). Thus the selection is for growth in the absence of histidine. Since only a few molecules per cell of IGP dehydratase are required for histidine prototrophy, the assay is very sensitive.

In a more complex version of the assay, cells can be selected for resistance to aminotriazole (AT), a drug that inhibits the activity of IGP dehydratase. Cells with low, fixed level of expression of HIS3 are sensitive to the drug, while cells with higher levels are resistant. The amount of AT can be selected to inhibit cells with a basal level of HIS3 expression (whatever that level is) but allow growth of cells with an induced level of expression. In this case selection is for growth in the absence of histidine and in the presence of a suitable level of AT.

The marker gene may also be a screenable gene. The screened characteristic may be a change in cell morphology, metabolism or other screenable features. Suitable markers include beta-galactosidase (X-gal, $C_{12}$FDG, Salmon-gal, Magenta-gal (latter two from Biosynth Ag), alkaline phosphatase, horseradish peroxidase, exo-glucanase (product of yeast exb1 gene; nonessential, secreted); luciferase; bacterial green fluorescent protein; (human placental) secreted alkaline phosphatase (SEAP); and chloramphenicol transferase (CAT). Some of the above can be engineered so that they are secreted (although not β-galactosidase). A preferred screenable marker gene is beta-galactosidase; yeast cells expressing the enzyme convert the colorless substrate X-gal into a blue pigment.

In still another embodiment, the host cell is a pigment cell line capable of dispersing or aggregating its pigment in response to activation of a receptor or ion channel. See, for example, U.S. Pat. No. 6,051,386. In particular, a pigment disperse assay can be generated by expression of a recombinant receptor or ion channel in a pigment-containing host cell. Activating mutants can be identified by changes in the rate of pigment dispersion (or aggregation as the case may be). In preferred embodiments, an imaging system, e.g., a computer guided video system, or even photographs, can be used to identify pigment cells that disperse or aggregate their pigment.

The first step in developing a melanophore based methodology for studying the affects of mutations on receptor activation is to express the receptor in the appropriate cells. Several promoters and procedures for DNA transfection have been tested for their ability to be used by frog melanophores to express foreign cDNAs. The tested promoters include ones from CMV (cytomegalovirus), RSV (Rous sarcoma virus), frog heat shock, SV40 early and frog beta-actin while the tested methods of introducing DNA into the cells that have been evaluated include calcium phosphate precipitation, DEAF-dextran, lipofection and electroporation. The best combination appears to be the use of a CMV promoter to drive expression of the coding sequence along with electroporation.

A melanophore assay can be read with, for example, a standard 96 well plate reader. Although the ability of an activated receptor to induce pigment dispersion or aggregation within melanophores may be easily recognized by eye, for high through-put screening, quantitation of the degree of pigment dispersion, e.g., with a standard 96 well plate, is useful.

I. Pharmaceutical Preparations of Identified Agents

As set out above, once identified as an activating mutation, the mutant receptor can then be used to screen for compounds which inhibit the phenotype conferred by the activation of the receptor or ion channel. Thus, the present invention specifically contemplates an assay system including a host cell expressing the mutant receptor or ion channel. The cell is contacted with one or more test agents, and changes in the second messenger generation, expression of transcriptional targets or the like are detected.

Alternatively, second messengers and transcriptional targets which may be identified for the first time by the discovery of an activated form of the receptor can subsequently be used as reporters to screen for agonists of the wild-type receptor. Thus, the present invention specifically contemplates an assay system including a host cell expressing the wild-type receptor or ion channel. The cell is contacted with one or more test agents, and changes in a second messenger or expression of a transcriptional target identified from the activated mutant are detected.

After identifying certain test compounds in the subject assay, e.g., as potential agonists or antagonists of a receptor, the practitioner of the subject assay will continue to test the efficacy and specificity of the selected compounds both in vitro and in vivo. Whether for subsequent in vivo testing, or for administration to an animal as an approved drug, agents identified in the subject assay can be formulated in pharmaceutical preparations for in vivo administration to an animal, preferably a human.

The compounds selected in the subject assay, or a pharmaceutically acceptable salt thereof, may accordingly be formulated for administration with a biologically acceptable medium, such as water, buffered saline, polyol (for example, glycerol, propylene glycol, liquid polyethylene glycol and the like) or suitable mixtures thereof. The optimum concentration of the active ingredient(s) in the chosen medium can be determined empirically, according to procedures well known to medicinal chemists. As used herein, "biologically acceptable medium" includes any and all solvents, dispersion media, and the like which may be appropriate for the desired route of administration of the pharmaceutical preparation. The use of such media for pharmaceutically active substances is known in the art. Except insofar as any conventional media or agent is incompatible with the activity of the compound, its use in the pharmaceutical preparation of the invention is contemplated. Suitable vehicles and their formulation inclusive of other proteins are described, for example, in the book Remington's Pharmaceutical Sciences (Remington's Pharmaceutical Sciences. Mack Publishing Company, Easton, Pa., USA 1985). These vehicles include injectable "deposit formulations". Based on the above, such pharmaceutical formulations include, although not exclusively, solutions or freeze-dried powders of the compound in association with one or more pharmaceutically acceptable vehicles or diluents, and contained in buffered media at a suitable pH and isosmotic with physiological fluids. In preferred embodiment, the compound can be disposed in a sterile preparation for topical and/or systemic administration. In the case of freeze-dried preparations, supporting excipients such as, but not exclusively, mannitol or glycine may be used and appropriate buffered solutions of the desired volume will be provided so as to obtain adequate isotonic buffered solutions of the desired pH. Similar solutions may also be used for the pharmaceutical compositions of compounds in isotonic solutions of the desired volume and include, but not exclusively, the use of buffered saline solutions with phosphate or citrate at suitable concentrations so as to obtain at all times isotonic pharmaceutical preparations of the desired pH, (for example, neutral pH).

We claim:

1. A method for identifying constitutively activating mutations in an orphan receptor or an ion channel, comprising:
   (a) identifying small or medium side-chain amino acid residues of a candidate orphan receptor that are located in or proximate to a transmembrane segment of the orphan receptor;
   (b) providing a library of coding sequences for potentially activating mutations of the candidate orphan receptor or ion channel, wherein said library is generated by replacing only coding sequences for the identified small or medium side-chain amino acids with coding sequences for large side-chain amino acids, wherein the mutation is conservative with respect to charge;
   (c) expressing the library in mammalian host cells;
   (d) measuring an activity of the encoded receptor or ion channel in the mammalian host cells; and
   (e) identifying those coding sequence(s) which encoded activated receptors or ion channels.

2. The method of claim 1, wherein the receptor is a multipass transmembrane receptor.

3. The method of claim 2, wherein the receptor is a seven transmembrane (7TM) receptor selected from the group consisting of: a G-protein coupled receptor, a chemoattractant peptide receptor, a neuropeptide receptor, a light receptor, a neurotransmitter receptor, and a polypeptide hormone receptor.

4. The method of claim 1, wherein the activity is measured directly by determining the level of second messengers generated in response to receptor or ion channel activation.

5. The method of claim 1, wherein the activity is measured indirectly by determining the level of transcription from an indicator gene.

6. The method of claim 5, wherein the indicator gene is an unmodified endogenous gene.

7. The method of claim 5, wherein the indicator gene is a heterologous reporter gene, the activation of the transcriptional regulatory element of which is directly or indirectly regulated by the receptor or ion channel.

8. The method of claim 7, wherein the reporter gene encodes a gene product selected from the group consisting of: chloramphenicol acetyl transferase, beta-galactosidase, secreted alkaline phosphatase, a gene product which confers a growth signal, and a gene product for growth in media containing aminotriazole or canavanine.

9. The method of claim 6 or 7, wherein the level of transcriptional activation of the indicator gene is amplified by overexpressing one or more intermediate components of the signaling cascade leading to the activation of the indicator gene.

10. The method of claim 5, wherein the sensitivity of the indicator gene is modified by manipulating the promoter sequence at the natural locus for the indicator gene.

11. The method of claim 5, wherein the activity of the indicator gene is modified by manipulating the transcriptional regulatory sequence at the natural locus for the indicator gene.

12. The method of claim 5, wherein the activity of the indicator gene is modified by replacing the transcriptional regulatory sequence of the indicator gene with that of a heterologous gene.

13. The method of any one of claim 7, 11, or 12, wherein the transcriptional regulatory element is derived from that of immediate early genes.

14. The method of any one of claim 7, 11, or 12, wherein the transcriptional regulatory element is derived from several heterologous genes.

15. The method of claim 1, wherein the small or medium side-chain amino acids are located at the interfaces between transmembrane helices.

16. The method of claim 1, wherein the small or medium side-chain amino acids are selected from the group consisting of: glycine, alanine, and serine.

17. The method of claim 1, wherein the small or medium side-chain amino acids are selected from the group consisting of: asparagine, aspartic acid, cysteine, proline, threonine and valine.

18. The method of claim 1, wherein the large side-chain amino acids are selected from the group consisting of: tryptophane, leucine, histidine, threonine, and tyrosine.

19. The method of claim 1, wherein the large side-chain amino acids are selected from the group consisting of: asparagine, cysteine, glutamine, isoleucine, methionine, phenylalanine, proline, and valine.

20. The method of claim 1, wherein the cell is a pigment cell capable of dispersing or aggregating its pigment in response to an activated receptor or ion channel.

21. The method of claim 1, wherein the mutation is identified as an activating mutation if the activity of the mutant polypeptide increases by at least 2-fold when compared to the activity of the wild-type polypeptide.

22. The method of claim 1, wherein the mutation is identified as an activating mutation if the activity of the mutant polypeptide increases by at least 5-fold when compared to the activity of the wild-type polypeptide.

23. The method of claim 1, wherein the mutation is identified as an activating mutation if the activity of the mutant polypeptide increases by at least 10-fold when compared to the activity of the wild-type polypeptide.

24. A method for identifying constitutively activating mutations in an orphan multipass transmembrane receptor, comprising:
  (a) identifying small or medium side-chain amino acid residues of a candidate orphan multipass transmembrane receptor that are located in or proximate to a transmembrane segment of the receptor;
  (b) providing a library of coding sequences for the multipass transmembrane receptor, wherein said library includes variant sequences which differ from the wild-type sequence of the receptor by one or more point mutations at only the identified amino acid residues from (a), wherein the mutations are conservative with respect to charge;
  (c) expressing the library in mammalian host cells;
  (d) measuring the activity of the encoded multipass transmembrane receptor in the mammalian host cells; and
  (e) identifying constitutively activating mutations in said orphan multipass transmembrane receptor.

* * * * *